(12) United States Patent
Maliga et al.

(10) Patent No.: US 6,297,054 B1
(45) Date of Patent: Oct. 2, 2001

(54) EDITING-BASED SELECTABLE PLASTID MARKER GENES

(75) Inventors: Pal Maliga, East Brunswick, NJ (US); Helaine Carrer, Piracicaba (BR); Sumita Chaudhuri, Davis, CA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/202,316

(22) PCT Filed: Jun. 13, 1997

(86) PCT No.: PCT/US97/10318

§ 371 Date: Jun. 1, 1999

§ 102(e) Date: Jun. 1, 1999

(87) PCT Pub. No.: WO97/47771

PCT Pub. Date: Dec. 18, 1997

Related U.S. Application Data

(60) Provisional application No. 60/019,741, filed on Jun. 14, 1996.

(51) Int. Cl.$^7$ .............................. C12N 15/82; C07H 21/04
(52) U.S. Cl. ............................................ 435/468; 536/23.1
(58) Field of Search ........................... 435/6, 468; 11/11; 800/295; 536/23.1

(56) References Cited

U.S. PATENT DOCUMENTS

| | | | |
|---|---|---|---|
| 5,451,513 | 9/1995 | Maliga et al. | 800/278 |
| 5,877,402 | 3/1999 | Maliga et al. | 800/298 |

OTHER PUBLICATIONS

Elizabeth H. Harris, et al. Antibiotic Resistance Mutations in the Chloroplast 16S and 23S rRNA Genes of Chlamydomonas reinhardtii: Correlation of Genetic and Physical Maps of the Chloroplast Genome. Genetics 123: 281–292 (Oct. 1989).

Sumita Chaudhuri, et al. Site–specific factor involved in the editing of the psbL mRNA in tobacco plastids. The EMBO Journal. vol. 14, No. 12: 2951–2957 (1995).

(List continued on next page.)

Primary Examiner—Robert A. Schwartzman
Assistant Examiner—Katharine F Davis
(74) Attorney, Agent, or Firm—Dann, Dorfman, Herrell and Skillman

(57) ABSTRACT

Disclosed are novel DNA constructs for selecting plastid transformants in higher plants. Also disclosed are editing based selectable marker genes which require editing at the transcriptional level for expression of the selectable marker gene. Vectors including such edited upstream sequences operably linked to slectable marker genes facilitate the isolation of plastid, rather than nuclear transformants in higher plants.

17 Claims, 18 Drawing Sheets

OTHER PUBLICATIONS

Hillel Fromm, et al. The molecular basis for rRNA–dependent spectinomycin resistance in Nicotiana chloroplasts. The EMBO Journal vol. 6, No. 11: 3233–3237 (1987).

Wilhelm Gruissem. Chloroplast Gene Expression: How Plants Turn Their Plastids On. Cell 56:161–170 (Jan. 27, 1989).

Pal Maliga, et al. Plastid engineering in land plants: a conservative genome is open to change. Phil. Trans. R. Soc. Lond. B 342: 203–208 (1993).

J.–D.Rochaix. Post–Transcriptional Steps in the Expression of Chloroplast Genes. Annu. Rev. Cell Biol. 8:1–28 (1992).

Kurt Weising, et al. Foreign Genes in Plants: Transfer, Structure, Expression, and Applications. Annu. Rev. Genet. 22: 421–77 (1988).

Hans Kossel, et al. RNA Editing in Chloroplasts of Higher Plants. Plant Mitochondria (Brennicke, A, and Kuck, U. eds.) VCH Verlagsgesellschaft mbH, Weinheim (Germany) (1993).

Pal Maliga. Towards Plastid Transformation in Flowering Plants. Tibtech vol. 11 (Mar. 1993).

Ralph Bock, et al. Introduction of a heterologous editing site into the tobacco plastid genome: the lack of RNA editing leads to a mutant phenotype. The EMBO Journal. vol. 13, No. 19: 4623–4628 (1994).

Ralph Bock, et al. In vivo testing of a tobacco plastid DNA segment for guide RNA function in psbL eidting. Mol. Gen Genet 247:439–443 (1995).

Zora Svab, et al. High–frequency plastid transformation in tobacco by selection for a chimeric aadA gene. Proc. Natl. Acad. Sci. USA 90:913–917 (Feb. 1993).

Chaudhuri et al. The EMBO Journal 14(12):2951–2957 1995.*

Bock et al., EMBO J. 13: 4623–4628, Introduction of a heterologous editing site into the tobacco plastid genome: the lack of RNA editing leads to a mutant phenotype.*

Bock, et al., Mol. Gen. Genet. 247: 439–443, In vivo testing of a tobacco plastid DNA segment for guide RNA function in psbl editing.*

* cited by examiner

SEQUENCE LISTING

```
<160> NUMBER OF SEQ ID NOS: 60

<210> SEQ ID NO 1
<211> LENGTH: 259
<212> TYPE: DNA
<213> ORGANISM: Nicotiana tabacum

<400> SEQUENCE: 1
atgactatag atcgaaccta tccaattttt acagtacgat ggttggctgt tcacggccta      60
gctgtaccta ccgtcttttt tttgggatca atatcagcaa tgcagttcat ccaacgataa     120
acttaatccg aattatagag ctacgacaca atcaaacccg aacgaacaaa atgttgaatt     180
gaatcgtacc agtctctact gggggttatt actcattttt gtacttgctg ttttattttc     240
caattatttc ttcaattaa                                                  259

<210> SEQ ID NO 2
<211> LENGTH: 39
<212> TYPE: PRT
<213> ORGANISM: Nicotiana tabacum

<400> SEQUENCE: 2

Met Thr Ile Asp Arg Thr Tyr Pro Ile Phe Thr Val Arg Trp Leu Ala
  1               5                  10                  15

Val His Gly Leu Ala Val Pro Thr Val Phe Phe Leu Gly Ser Ile Ser
             20                  25                  30

Ala Met Gln Phe Ile Gln Arg
         35

<210> SEQ ID NO 3
<211> LENGTH: 38
<212> TYPE: PRT
<213> ORGANISM: Nicotiana tabacum

<400> SEQUENCE: 3

Met Thr Gln Ser Asn Pro Asn Glu Gln Asn Val Glu Leu Asn Arg Thr
  1               5                  10                  15

Ser Leu Tyr Trp Gly Leu Leu Leu Ile Phe Val Leu Ala Val Leu Phe
             20                  25                  30

Ser Asn Tyr Phe Phe Asn
         35

<210> SEQ ID NO 4
<211> LENGTH: 300
<212> TYPE: DNA
<213> ORGANISM: Artificial Sequence
<220> FEATURE:
<223> OTHER INFORMATION: Synthetic Sequence

<400> SEQUENCE: 4
gagctcggta cccaaagctc ccccgccgtc gttcaatgag aatggataag aggctcgtgg      60
```

```
gattgacgtg aggggggcagg gatggctata tttctgggag cgaactccgg gcgaatacga      120
agcgcttgga tacagttgta gggagggatc catgactttg ggatcaatat cagcaatgca      180
gttcatccaa cgataaactt aatccgaatt atagagctac gacacaatca aacccgaacg      240
aacaaaatgt tgaaggggaa gcggtgatcg ccgaagtatc gactcaacta tcagaggtag      300
```

```
<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 5

Met Thr Leu Gly Ser Ile Ser Ala Met Gln Phe Ile Gln Arg
 1               5                  10
```

```
<210> SEQ ID NO 6
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 6

Met Thr Gln Ser Asn Pro Asn Glu Gln Asn Val Glu Gly Glu Ala Val
 1               5                  10                  15

Ile Ala Glu Val Ser Thr Gln Leu Ser Glu Val
            20                  25
```

```
<210> SEQ ID NO 7
<211> LENGTH: 300
<212> TYPE: DNA
<213> ORGANISM: Artificial Sequence
<220> FEATURE:
<223> OTHER INFORMATION: Synthetic Sequence

<400> SEQUENCE: 7
gagctcggta cccaaagctc ccccgccgtc gttcaatgag aatggataag aggctcgtgg       60
gattgacgtg aggggggcagg gatggctata tttctgggag cgaactccgg gcgaatacga     120
agcgcttgga tacagttgta gggagggatc catgactttg ggatcaatat cagcaatgca     180
gttcatccaa cgataaactt aatccgaatt atagagctac gacacaatca aacccgaacg     240
aacaaaatgt tgaattgggg attgaacaag atggattgca cgcaggttct ccggccgctt     300
```

```
<210> SEQ ID NO 8
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 8

Met Thr Gln Ser Asn Pro Asn Glu Gln Asn Val Glu Leu Gly Ile Glu
 1               5                  10                  15

Gln Asp Gly Leu His Ala Gly Ser Pro Ala Ala Trp
            20                  25
```

```
<210> SEQ ID NO 9
<211> LENGTH: 18
<212> TYPE: PRT
<213> ORGANISM: Artificial Sequence
```

```
<220> FEATURE:
<223> OTHER INFORMATION: Synthetic Sequence

<400> SEQUENCE: 9

Met Leu Asn Trp Gly Leu Asn Lys Met Asp Cys Thr Gln Val Leu Arg
 1               5                  10                  15

Pro Leu

<210> SEQ ID NO 11
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 10
ccgaattata gagctacgac ac                                              22

<210> SEQ ID NO 11
<211> LENGTH: 180
<212> TYPE: DNA
<213> ORGANISM: Nicotiana tabacum

<400> SEQUENCE: 11
aatattttga gcacgggttt ttatggtcca agtgtatctt gtctttacta cgaattattt      60
tccttggtta acaataattg tagttttttcc aatatttgcg ggttccttaa ttttctttct   120
tccccataaa ggaaataggg taattaggtg gtatacgata tgtatatgta ttttagaact    180

<210> SEQ ID NO 12
<211> LENGTH: 43
<212> TYPE: PRT
<213> ORGANISM: Nicotiana tabacum

<400> SEQUENCE: 12

Met Asn Tyr Phe Pro Trp Leu Thr Ile Ile Val Val Phe Pro Ile Phe
 1               5                  10                  15

Ala Gly Ser Leu Ile Phe Phe Leu Pro His Lys Gly Asn Arg Val Ile
            20                  25                  30

Arg Trp Tyr Thr Ile Cys Ile Cys Ile Leu Glu
            35                  40

<210> SEQ ID NO 13
<211> LENGTH: 171
<212> TYPE: DNA
<213> ORGANISM: Maize

<400> SEQUENCE: 13
tccacttcta gatagagaaa cgaactaaag gagaatactt aataatacgg cgaaacattt      60
atacaaaaca cctatcccga gcacacgcaa gggaaccgta gacaggcaag tgaaatccaa    120
tccacgaaat aaattgatcc atggacggca ccgttgtggt aaaggtcgta a              171

<210> SEQ ID NO 14
<211> LENGTH: 41
<212> TYPE: PRT
<213> ORGANISM: Maize

<400> SEQUENCE: 14

Met Ala Lys His Leu Tyr Lys Thr Pro Ile Pro Ser Thr Arg Lys Gly
 1               5                  10                  15

Thr Val Asp Arg Gln Val Lys Ser Asn Pro Arg Asn Lys Leu Ile His
```

```
            20                  25                  30
Gly Arg His Arg Cys Gly Lys Gly Arg
        35                  40
```

<210> SEQ ID NO 15
<211> LENGTH: 72
<212> TYPE: DNA
<213> ORGANISM: Artificial Sequence
<220> FEATURE:
<223> OTHER INFORMATION: Synthetic Sequence

<400> SEQUENCE: 15

```
cattcatgac tttgggatca atatcagcat atgcagttca tccaacgata aacttaatcc      60
gaattataga gc                                                         72
```

<210> SEQ ID NO 16
<211> LENGTH: 71
<212> TYPE: DNA
<213> ORGANISM: Artificial Sequence
<220> FEATURE:
<223> OTHER INFORMATION: Synthetic Sequence

<400> SEQUENCE: 16

```
cggtctgaat tcaattcaac attttgttcg ttcgggtttg attgtgtcgt agctctataa      60
ttcggattaa g                                                          71
```

<210> SEQ ID NO 17
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 17

```
caatatcagc aatgcagttc atcc                                            24
```

<210> SEQ ID NO 18
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 18

```
ccaagcgatc ttcttcttgt ccaa                                            24
```

<210> SEQ ID NO 19
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 19

```
gcgctcgatg acgccaac                                                   18
```

<210> SEQ ID NO 20
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 20

```
cacgacgaga tcctcgccg                                              19

<210> SEQ ID NO 21
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 21
gaatagcctc tccaccca                                               18

<210> SEQ ID NO 22
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 22
ggaatccttc cagtagtatc ggcc                                        24

<210> SEQ ID NO 23
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 23
ggaaaataaa acagcaagta c                                           21

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 24
caaatattgc aaagtcccgg                                             20

<210> SEQ ID NO 25
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 25
ccggatcgcc acctacac                                               18

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
tggctataac agagtttctc                                             20

<210> SEQ ID NO 27
<211> LENGTH: 21
<212> TYPE: DNA
<213> ORGANISM: Artificial Sequence
```

-continued

```
<220> FEATURE:
<223> OTHER INFORMATION: Synthetic Sequence

<400> SEQUENCE: 27
ggatttccag aagaagatgc c                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 28
gttcgttcgg gtttgattgt g                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 29
gaactcaacg ggcccttccc c                                              21

<210> SEQ ID NO 30
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 30
ggagggaagt ggagtaaatg gccg                                           24

<210> SEQ ID NO 31
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 31
aattcgaagc gcttggatac agttgtaggg a                                   31

<210> SEQ ID NO 32
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 32
gtaagagatg tgaatccgcc tgt                                            23

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
gcataagtcg ttagaaggag                                                20
```

<210> SEQ ID NO 34
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 34
gaagaaagaa aattaaggaa cc                                                22

<210> SEQ ID NO 35
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 35
catgccatgg ctagcattga acaagatgga ttgcacg                                37

<210> SEQ ID NO 36
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 36
gtactctaga cccgctcaga agaactcg                                          28

<210> SEQ ID NO 37
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 37
ctagccatgg ctttgggatc aatatcagca atg                                    33

<210> SEQ ID NO 38
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 38
ctagccatgg catcagcaat gcagttcatc c                                      31

<210> SEQ ID NO 39
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 39
ctagccatgg cgttcatcca acgataaact taa                                    33

<210> SEQ ID NO 40
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 40
ctagccatgg cataaactta atccgaatta tagag                                   35

<210> SEQ ID NO 41
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 41
ctagccatgg ccgaattata gagctacgac ac                                      32

<210> SEQ ID NO 42
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 42
ctagccatgg ctacgacaca atcaaacccg a                                       31

<210> SEQ ID NO 43
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 43
ctagctagct tcaacatttt gttcgttcgg                                         30

<210> SEQ ID NO 44
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 44
ctagctagct tcgttcgggt ttgattgtg                                          29

<210> SEQ ID NO 45
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 45
ctagctagct gattgtgtcg tagctctata                                         30

<210> SEQ ID NO 46
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 46
ctagctagcc gtagctctat aattcggatt                                         30

<210> SEQ ID NO 47

```
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 47
ctagccatgg tatagagcta cgacac                                           26

<210> SEQ ID NO 48
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 48
ctagctagca agtgtcgtag ctctata                                          27

<210> SEQ ID NO 49
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 49
aattatagag ctccgacaca atc                                              23

<210> SEQ ID NO 50
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 50
aattatagag ctaccacaca atc                                              23

<210> SEQ ID NO 51
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 51
ctagccatgg tattttgagc acgggttttt ctggtcc                               37

<210> SEQ ID NO 52
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 52
ctagctagct ggaaaaacta caattattgt taacc                                 35

<210> SEQ ID NO 53
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 53
```

```
ctagccatgg aaacgaacta aaggagaata c                                    31
```

<210> SEQ ID NO 54
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 54

```
ctagctagcc gggataggtg ttttgtataa a                                    31
```

<210> SEQ ID NO 55
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 55

```
atggcagcta ct                                                         12
```

<210> SEQ ID NO 56
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 56

```
ctagccatgg cagctactct aggggaatg                                       30
```

<210> SEQ ID NO 57
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 57

```
ctagtctaga cgtatacgtc aggagtcca                                       29
```

<210> SEQ ID NO 58
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 58

```
atggtcccgg t                                                          11
```

<210> SEQ ID NO 59
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 59

```
ctagccatgg gtcccggtat ttattaccg                                       29
```

<210> SEQ ID NO 60
<211> LENGTH: 34
<212> TYPE: DNA

-continued

```
<213> ORGANISM: Artificial Sequence
<220> FEATURE:
<223> OTHER INFORMATION: Synthetic Sequence

<400> SEQUENCE: 60
ctaggtcgac ttaggcattt tcttttgacc caat                            34
```

EDITING-BASED SELECTABLE PLASTID MARKER GENES

This application claims priority under 35 U.S.C. §119(e) to U.S. Provisional Application No. 60/019,741 filed Jun. 14, 1996.

Pursuant to 35 U.S.C. §202(c), it is hereby acknowledged that the U.S. Government has certain rights in the invention described herein, which was made in part with funds from the National Science Foundation.

FIELD OF THE INVENTION

This invention relates to the field of plant molecular biology. Specifically, DNA constructs are provided that facilitate the selection of stably transformed plastids in multicellular plants for which the encoded RNA is modified post-transcriptionally.

BACKGROUND OF THE INVENTION

Several publications are referenced in this application by author names and year of publication in parenthesis in order to more fully describe the state of the art to which this invention pertains. Full citations for these references are found at the end of the specification. The disclosure of each of these publications is incorporated by reference herein.

Genetic engineering of plants involves the development and application of technology for genetic transformation through the direct manipulation of the plant genome and plant gene expression by the introduction of novel DNA. One method of transformation employs a derivative of the tumor inducing (Ti) plasmid from the bacterium, *Agrobacterium tumefaciens*. Other methods utilize direct gene transfer into protoplasts using biolistics, electroporation, polyethylene glycol treatment.

While the incorporation of transforming DNA in the nucleus of plant cells is well known to those skilled in the art, transformation protocols that selectively identify transformed plastid DNA, to the exclusion of other genetic compartments have not yet been described. With the above-described methods, if plastid transformation only is desired, nuclear transformants may express the gene encoding the selectable marker and result in the generation of false positives.

The need for plastid-specific marker genes is based on this observation. In earlier work, selection for kanamycin resistance of pTNH32-bombarded tobacco leaves yielded a large number of nuclear transformants (Carrer et al., 1993). Indeed, recovery of nuclear gene transformants with other plastid kan genes (Cornelissen and Vandewiele 1989), and with promoterless kan constructs (Koncz et al. 1989) confirms that kanamycin resistant clones may be readily obtained by transformation with constructs that were not designed for expression in the nucleus. Additionally, nuclear gene transformants in tobacco may also be recovered by selection for spectinomycin resistance genes designed for expression in plastids.

Given the large number of plastid genomes in plant cells, the ability to select for the transformed genome in culture is a key element in achieving successful transformation. Selection markers have been identified by screening cultured plant cells for mutants resistant to various substances, such as antibiotics and herbicides. Such antibiotics and herbicides are listed in Table I, below. However, to date, a method has not been developed that will facilitate plastid transformation with the concomitant exclusion of the selection of nuclear transformants. The development of such a system minimizes the false positives that result when a nuclear transformation event occurs.

RNA editing is a process that post-transcriptionally alters RNA sequences. Until recently, it was believed that chloroplasts, in contrast to mitochondria, did not utilize RNA editing and that the prediction of amino acid sequences from the corresponding gene sequences was generally correct. While most chloroplast genes begin with the canonical ATG start codon, genes have been identified that encode an ACG at a position that corresponds to the 5' terminal ATG in homologous genes in other species. Recently it has been shown that this ACG codon is not conserved at the mRNA level. It is converted to a functional AUG codon by C to U editing (Hoch et al., 1991). Most of the edited codons found to date, restore amino acids that are conserved in the corresponding peptides from chloroplasts of other species. This editing process is plastid specific. Genes edited in the plastid are not edited in the nucleus or other organelles of the plant. The present invention provides DNA constructs and methods to facilitate the selection of stably transformed plastids, based upon a requirement for RNA editing in the transforming constructs which occurs exclusively in the plastid. Targeted manipulation of the plastid genome can now be performed with greater ease. Such manipulations include gene replacement, gene deletion, insertion of foreign genes and expression of recombinant proteins in plastids.

SUMMARY OF THE INVENTION

This invention provides DNA constructs and methods for the selection of stably transformed plastids of multicellular plants. The DNA constructs of the invention can be used for the exclusive selection of plastid transformants. Nuclear transformants will not be selected with the constructs of the instant invention.

According to one aspect of the invention, chimeric DNA constructs are described containing an edited gene segment translationally fused to a selectable marker gene. Following editing at the RNA level, which occurs in the plastid, the selectable marker gene is expressed. Cells or tissues are maintained on the selection medium until they have reached a homoplasmic condition, in which substantially all of the plastids of the cell or tissue have been transformed.

In a preferred embodiment of the invention, the above described chimeric construct is incorporated into a vector containing the necessary homologous sequences for targeted integration into the plastid genome. The targeting segment is of sufficient size to promote homologous recombination with a pre-determined plastid genome sequence, thereby replacing that sequence in the genome of the transformed plastid. The vector may further comprise a foreign gene of interest to beneficially augment the phenotype of the plant. In yet another embodiment of the invention, the chimeric DNA constructs may contain sequences that direct tissue specific regulation of the foreign gene of interest.

The method of the present invention is generally applicable to the selection of stably transformed plastids in both monocotyledonous and dicotyledonous plants. Following selection, the cells or tissues expressing the selectable phenotype are regenerated into multicellular plants.

BRIEF DESCRIPTION OF THE DRAWINGS

FIG. 3A shows PCR amplification products from DNA (lanes 1, 5) and cDNA (lanes 2, 6) with primers O1 and O2 (SEQ ID NOS: 17 and 18) for EaadA, and primers O1 and O4 (SEQ ID NOS: 17 and 20) for Ekan templates. The location of primers is shown in FIGS. 2A & 2B. Controls were amplification reactions carried out with DNase I-treated RNA (lanes 3, 7) and buffer only (lanes 4 and 8) using the same primers. FIG. 3B shows the DNA and cDNA sequence of EaadA in the Nt-pHC94-1 plant, and FIG. 3C shows Ekan in the Nt-pJLM23-2 plant. The amplified products were directly sequenced with primers O3 (EaadA); SEQ ID NO: 19 and O5 (Ekan); SEQ ID NO: 21. Due to the polarity of primers, the sequence shown is complementary to the mRNA. The editing site in the sequence is marked by an arrowhead. Note a mixture of A and G nucleotides at the editing site in the cDNA samples indicating partial editing.

FIG. 4A depicts the PCR amplification products from DNA (lanes 1, 5, 9) and cDNA (lanes 2, 6, 10) from wild-type, Nt-pHC94-1 (EaadA) and Nt-pJLM23-2 (Ekan) plants with primers O1 and O6 (SEQ ID NOS: 17 and 22). See FIG. 1. Controls were amplification reactions carried out with DNase I-treated RNA (lanes 3, 7, 11) and buffer only (lanes 4, 8, 12). The DNA and cDNA sequence of psbL in wild-type is shown in FIG. 4B. FIG. 4C shows the sequences in Nt-pHC94-1 (EaadA). FIG. 4D shows the sequences in Nt-pJLM23-2 (Ekan) plants. The amplified products were directly sequenced with primer O7 (SEQ ID NO: 23). The sequence shown is complementary to the mRNA sequence due to the polarity of the O7 primer (SEQ ID NO: 23). The editing site is indicated by an arrowhead. Note nearly complete editing in the wild type (G* is very faint) and partial editing in the transgenic plants.

FIG. 5A depicts a partial map of the plastid genome with the EaadA and Ekan genes obtained by transformation with the pHC94 or pJLM23 plasmids. The 16SrDNA and trnV genes, and the rps12/7 operon are marked. Horizontal arrows indicate mRNAs detected by the O14 oligonucleotide probe (SEQ ID NO: 28). The autoradiogram in the upper panel in FIG. 5B shows that the O14 oligonucleotide (SEQ ID NO: 28) detects the similar size (1.1-kb) psbE, EaadA and Ekan, and the 2.2-kb Ekan-aadA transcripts. Additional, minor uncharacterized RNA species are also visible which were not included in the quantitation. Total cellular RNA (2 μg per lane) was loaded from a wild-type plant (Wt), plasmid pHC94-transformed plants (Nt-pHC94-1, Nt-pHC94-11, Nt-pHC94-21) and plasmid pJLM23-transformed plants (Nt-pJLM23-2, Nt-pJLM23-14, Nt-pJLM23-18). The lower panel in FIG. 5B illustrates the accumulation of psbE mRNA detected by the psbJ probe, and of the 16S rRNA as the loading control. The filter was stripped of the labeled O14 oligonucleotide, and probed with a mixture of the psbJ and 16SrDNA probes. The psbE probe was obtained by PCR amplification of the psbJ region with primers O15 and O16 (SEQ ID NOS: 24 and 25) shown in FIG. 1. The 16SrDNA probe was a 2.4-kb EcoRI/EcoRV ptDNA fragment defined by the restriction sites at nucleotides 138448/141847 of the plastid genome (Shinozaki et al., 1986).

FIG. 7A shows the map of the chimeric ΔpsbL/kan gene, with the 98 nt ΔpsbF/Δpsb fragment (SEQ ID NO: 1) enlarged at the top. The positions of primers O4, O5 and O17 (SEQ ID NOS: 20, 21 and 31) are indicated. 66,780 and 66,683 are the nucleotides at the ends of the 98 nt ΔpsbF/ΔpsbL fragment (SEQ ID NO: 1) in the tobacco plastid genome (Shinozaki et al., 1986). The lower portion of FIG. 7A is a listing of pRV111A plasmid derivatives which carry chimeric ΔpsbL/kan genes. The nucleotide position at the end of the ΔpsbF/ΔpsbL deletion derivatives is given relative to the edited C (position O; arrow). The efficiency of editing of the chimeric ΔpsbL/kan mRNA (%), and the kanamycin resistance phenotype of the transgenic plants is listed. FIG. 7B is an autoradiogram demonstrating editing of the psbL site in the chimeric mRNAs. The cDNAs were PCR amplified with primers O17 and O4 (SEQ ID NOS: 31 and 21 respectively) and directly sequenced with primer O5 (SEQ ID NO: 21). Due to the polarity of O5 (SEQ ID NO: 21), the sequence shown is complementary to the mRNA. Accordingly, A at the edited position indicates a C to U conversion event and a G an unedited C nucleotide.

FIG. 9A shows the map of the psbE operon containing the psbL gene, with the position of oligonucleotides O1, O6 and O7 (SEQ ID NOS: 17, 22 and 23) used for PCR amplification and sequencing indicated. The 22 nt (−16/+5) sequence required for editing is shown. The edited C is marked by an arrow. The 16 nt segment competing for psbL-SEF is boxed. The plasmids used to obtain the transgenic plants are listed, as identified in FIGS. 7A and 7B and 8. Competition (+) was indicated by reduced editing efficiency of the psbL mRNA, as compared to nontransformed, wild-type plants. FIG. 9B is an autoradiogram showing editing of psbL mRNAs. The cDNAs were PCR amplified with primers 01 and 06 (SEQ ID NOS: 17 and 22) and directly sequenced with primer 07 (SEQ ID NO: 23). Due to the polarity of 07, the sequence shown is complementary to the mRNA. Accordingly, A at the edited position indicates a C to U conversion event and a G at the edited position, an unedited C nucleotide. A+G* denotes nearly complete editing (>99%) as in the wild-type plants. A+G denotes partial editing with ~10% unedited psbL transcripts.

FIG. 10A shows a partial map of the tobacco plastid genome containing the ndhD, psaC and ndhE genes, and the DNA sequence (SEQ ID NO: 11) with the edited ndhD translation initiation codon (underlined). The genes are marked and the DNA sequence is numbered according to Shinozaki et al., 1986. The ΔndhD segment (see SEQ ID NO: 11) in a dashed box was translationally fused with the kan gene, as shown in FIG. 10B. The position of primers 018, 019 and 020 (SEQ ID NOS: 32, 33 and 34) are indicated. The A nucleotide 26 bp upstream of the editing site (underlined) was changed to a C during construction of the chimeric gene. FIG. 10B shows the ΔndhD/kan chimeric gene in plasmid pSC23 expressed in the Prrn/Trps16 cassette. The positions of primers 04, 05 and 017 (SEQ ID NOS: 20, 21, and 31 respectively) are indicated. FIG. 10C depicts autoradiograms demonstrating editing of ndhD and psbL sites in wildtype (Nt-wt), Nt-pSC23 and Nt-pSC2 plants. Editing of the ndhD site was studied in the endogenous ndhD, and the chimeric ΔndhD/kan mRNAs. Editing of the psbL site was studied in the endogenous psbL, and the chimeric ΔpsbL/kan mRNAs. The ndhD cDNA was amplified with primers 018 and 019 (SEQ ID NOS: 32 and 33) and sequenced with primer 020 (SEQ ID NO: 34). The psbL cDNA was PCR amplified with primers 01 and 06 (SEQ ID NOS: 17 and 22) and directly sequenced with primer 07 (SEQ ID NO: 23). The ΔndhD/kan and ΔpsbL/kan cDNAs were amplified with primers 017 and 04 (SEQ ID NOS: 31 and 20), and sequenced with 05 (SEQ ID NO: 21). Due to the polarity of the sequencing primers, the sequence shown is complementary to the mRNA. Accordingly, A at the edited position indicates a C to U conversion event and a C, an unedited C nucleotide.

FIG. 11B demonstrates that the Δrpl2D/kan chimeric gene in plasmid pSC22 is expressed in the Prrn/Trps16 cassette. The position of primers O4, O5 and O17 (SEQ ID NOS: 20, 21 and 31) is indicated.

DETAILED DESCRIPTION OF THE INVENTION

Figure 1:
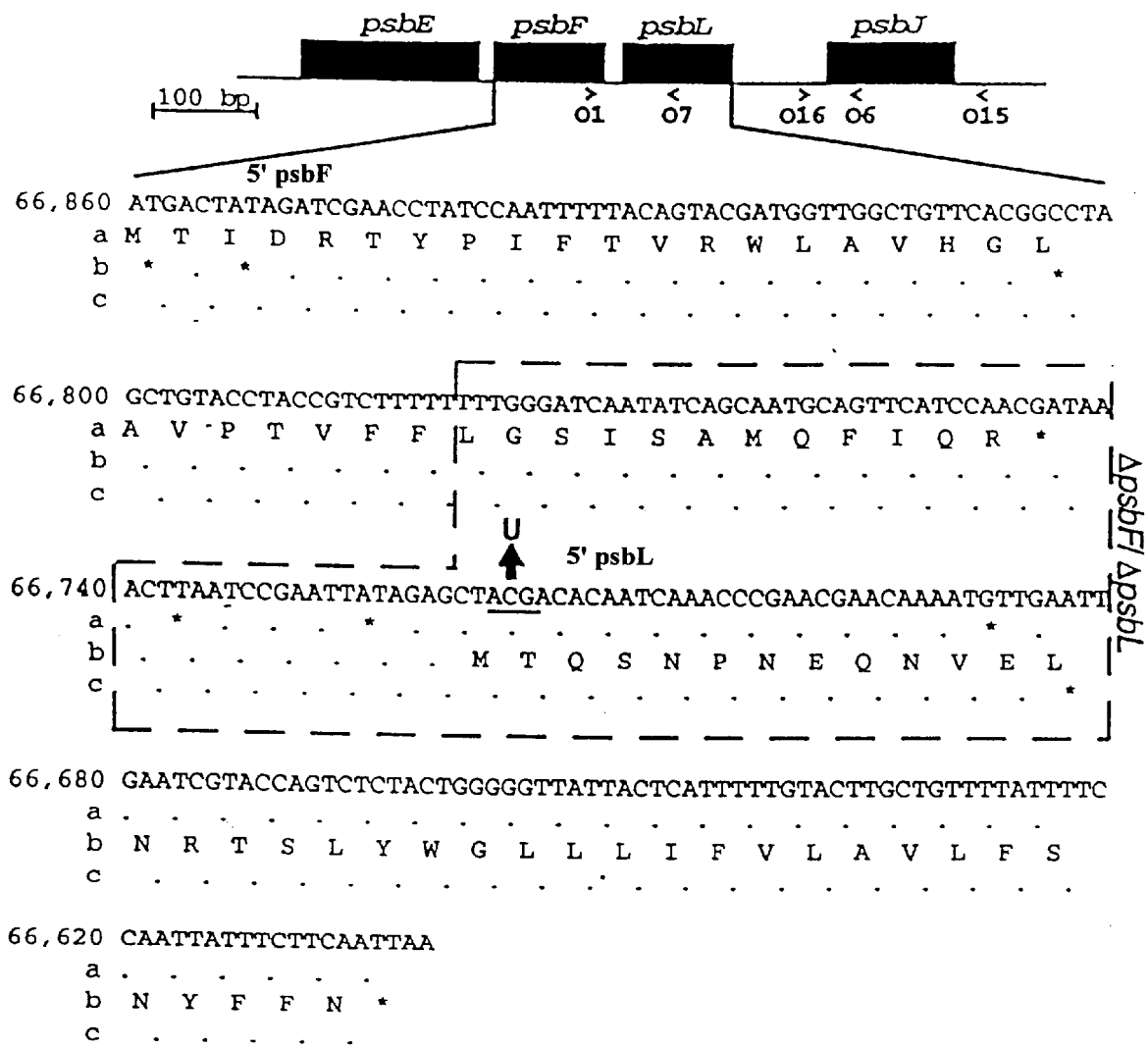
FIG. 1 is a schematic of the tobacco plastid psbE operon and the psbF and psbL DNA and amino acid sequences (SEQ ID NOS: 1, 2 and 3). The edited psbL initiation codon (from ACG to AUG) is underlined. The ΔpsbF/ΔpsbL region is bounded by dashed lines. The positions of oligonucleotides O1, O6, O7, O15 and O16 (SEQ ID NOS: 17, 22, 23, 29 and 30 respectively) are marked. The DNA sequence (SEQ ID NO: 1) is numbered according to Shinozaki et al. (1986).

In accordance with the present invention, methods and DNA constructs are provided to facilitate the selection of transformed plastids following delivery of transforming DNA. The constructs of the invention will be expressed only if they are appropriately edited at the RNA level within the plastid. In so far as it is known, the methods and DNA constructs described herein have heretofore been unavailable for multicellular plants.

The following definitions will facilitate the understanding of the subject matter of the present invention:

Heteroplasmic:

Refers to the presence of a mixed population of different plastid genomes within a single plastid or in a population of plastids contained in plant cells or tissues.

Homoplasmic:

Refers to a pure population of plastid genomes, either within a plastid or within a population contained in plant cells and tissues. Homoplasmic plastids, cells or tissues are genetically stable because they contain only one type of plastid genome. Hence, they remain homoplasmic even after the selection pressure has been removed, and selfed progeny are also homoplasmic. For purposes of the present invention, heteroplasmic populations of genomes that are functionally homoplasmic (i.e., contain only minor populations of wild-type DNA or transformed genomes with sequence variations) may be referred to herein as "functionally homoplasmic" or "substantially homoplasmic." These types of cells or tissues can be readily purified to homoplasmy by continued selection on the non-lethal selection medium. Most seed progeny of such plants are homoplasmic in the absence of selection pressure, due to random sorting of plastid genomes.

Plastome:

The genome of a plastid.

Transplastome:

A transformed plastid genome.

Transformation of Plastids:

Stable integration of transforming DNA into the plastid genome that is transmitted to the seed progeny of plants containing the transformed plastids.

Selectable Marker:

The term "selectable marker" refers to a phenotype that identifies a successfully transformed organelle, cell or tissue, when a gene or allele encoding the selectable marker is included in the foreign DNA used for transformation.

Transforming DNA:

Refers to homologous DNA, or heterologous DNA flanked by homologous DNA, which when introduced into plastids becomes part of the plastid genome by homologous recombination.

Edited Gene Segment:

Refers to a region of DNA which encodes an RNA which is post-transcriptionally altered.

Translationally Fused:

Refers to two coding regions of two separate genes spliced together in a construct such that both regions will be expressed at the protein level. In accordance with the present invention translation of the chimeric protein is dependent on appropriate editing of the upstream coding region at the mRNA level.

The detailed description as follows provides examples of preferred methods for making and using the DNA constructs of the present invention and for practicing the methods of the invention. Any molecular cloning and recombinant DNA techniques not specifically described are carried out by standard methods, as generally set forth, for example in Sambrook et al., "DNA Cloning, A Laboratory Manual," Cold Spring Harbor Laboratory, 1989.

In the detailed description and examples set forth hereinbelow, a preferred embodiment comprises a DNA segment that encodes an edited RNA segment operably linked to a second DNA segment which encodes a selectable marker. In the following examples tobacco chloroplasts are exemplified. Transformation vectors containing such combinations will be useful in enabling plastid-specific transformation. References made to positions and sequences on the tobacco chloroplast genome are taken from Shinozaki et al., EMBO J., 5: 2043–49 (1986), which discloses the complete nucleotide sequence of the Nicotiana tabacum chloroplast genome. Although tobacco is exemplified, it will be appreciated by those skilled in the art that the DNA constructs and methods of the present invention can be adapted to plastids of other plant species.

Plastid transformation requires: (1) a method for delivering DNA through the double membrane of the plastid; (2) integration of the heterologous DNA without interfering with the normal function of the plastid genome; and (3) efficient selection for the transplastome. Methodology for performing efficient transformation of plastids of multicellular plants is set forth in U.S. Pat. No. 5,451,513 issued Sep. 19, 1995, the entire disclosure of which is incorporated by reference herein.

In accordance with the present invention, it has been discovered that the selection criterion for identifying transplastomes is critical to the success of stable plastid transformation in higher plants. Accordingly, the selection technique of the present invention employs DNA encoding a selectable phenotype ("selectable marker") in the transforming DNA. Selection greatly facilitates obtaining transplastomic lines, due in part to the large number of identical plastid genome copies present in each plant cell (3,000–12,000 copies localized in up to 100 plastids in tobacco, as compared with 80 copies carried by a single plastid in Chlamydomonas). Selectable phenotypes can include antibiotic resistance, herbicide resistance, drug resistance or resistance to toxic analogs of metabolites.

The present invention provides selectable marker genes that require RNA-editing processes which occur in plastids only, not in the nucleus or in mitochondria. Such plastid specific marker genes will greatly enhance the ability to obtain stably transformed plastids in multicellular plants. The novel combination of plastid specific editing site controlling expression of a selectable marker is hereinafter described.

Certain mRNA sequences can be altered post-transcriptionally by a process known as RNA editing, so that their final nucleotide sequence differs from that encoded by the DNA sequence. The process has been detected in divergent organisms including trypanosomes, *Physarum polycephalum*, mammals, viruses and higher plants involving widely different molecular mechanisms (reviewed in Benne, 1994; Chan, 1993; Gray and Covello, 1993; Innerarity et al., 1996; Simpson and Thiemann, 1995).

In higher plants, editing of plastid and mitochondrial RNAs involves C to U conversions and rare cases of U to C changes in mitochondria. The number of editing sites in plastids is estimated to be about 25 (Maier et al., 1995) while in plant mitochondria it is 1000 or more (Schuster and Brennicke, 1994). Comparison of sequences surrounding editing sites have failed to identify any conserved primary sequence and/or structural motifs that could direct the site-selection process. The recent development of an in vitro editing system should lead to accelerated progress in the analysis of RNA editing in plant mitochondria (Araya et al., 1992; Yu and Schuster, 1995). Although an in vitro system for editing in plastids is still lacking, the availability of plastid transformation allows an in vivo approach to study plastid editing (Bock et al., 1994; Bock and Maliga, 1995; Sutton et al., 1995,.

While RNA editing has been reported to occur in plastids and mitochondria, it has not been observed in the nucleus (Kossel et al., 1993; Hanson et al., 1995). Furthermore, mitochondrial transcripts are not edited in plastids (Sutton et al., 1995). The discovery of RNA editing and the problem of recovering large numbers of nuclear transformants after bombardment of plant cells with plastid directed constructs, led to the design of the plastid transgenes of the invention which are expressed in plastids but not in other genetic compartments of the cell. The following examples describe the transgenes of the invention.

Briefly, one example of an editing based selectable marker gene utilizes the N-terminal segment of an edited plastid gene translationally fused to the coding region of an antibiotic resistance gene. The expression of the antibiotic resistance gene is dependent upon RNA editing of the construct. In a specific example, the N-terminal segment of psbL is fused to the coding region of aadA gene. Translation of the aadA gene is dependent on editing, and is used to recover plastid transformants by direct selection (Chaudhuri et al., 1995). Additionally, a psbL based editing selectable marker can comprise the similar ΔpsbL/kan chimeric gene (Chaudhuri and Maliga, 1996), in which kanamycin resistance is a reliable measure of the editing of the translation initiation codon (Chaudhuri et al., 1995; Chaudhuri and Maliga, 1996). Although these genes confer kanamycin resistance to the plant cell when present in each of the plastid genome copies in a cell, they could not be used for direct selection. Presumably this is because plastid transformants can only be directly selected by the kanamycin resistance marker if the chimeric genes are expressed at high levels. Direct selection for Ekan genes should be feasible by improving their expression level through appropriate engineering.

A second, novel example of an editing based selectable marker gene utilizes the ndhD edited segment. This construct, ΔndhD/kan was obtained by fusing the N-terminal segment of ndhD and the coding region of kan (Chaudhuri and Maliga, 1996). The above described selectable marker genes will facilitate the selection of transformants in certain dicot species.

A third type of editing based marker gene, Δrpl2/kan, is created by fusing the rpl2 edited segment to the kanamycin coding region. Such chimeric selectable marker genes will be used to advantage in selecting plastid transformants in monocots.

In tobacco plastids, functional psbL and ndhD mRNA is created by editing an ACG codon to an AUG translation initiation codon. To determine if editing may occur in a chimeric mRNA, the N-terminal part of psbL containing the editing site was translationally fused with the aadA and kan bacterial genes as described in the following examples. The chimeric constructs were introduced into the tobacco plastid genome by targeted gene insertion. Deletion derivatives of a 98 nt fragment (see SEQ ID NO: 1) were expressed as parts of chimeric transcripts to define the cis sequences required for psbL editing. In accordance with the instant invention, it has been found that a 22 nt fragment (SEQ ID NO: 10) is sufficient to direct psbL editing. Although the 22 nucleotides were required for editing, only 16 nucleotides competed for the psbL-specific editing factor.

Expression of the chimeric gene transcripts led to a significant decrease in the editing efficiency of the endogenous psbL mRNA. However, the efficiency of editing in the transplastomic lines was unchanged for four sites in the rpoB and ndhB mRNAs. Reduced efficiency of psbL editing, but not of the other four sites, in the transplastomic lines indicates depletion of psbL-specific editing factor(s). This finding implicates the involvement of site-specific factors in editing of plastid mRNAs in higher plants.

In addition to psbL, editing was shown to create the AUG translation initiation codon for ndhD in tobacco (Neckermann et al., 1994). To test whether editing of initiation codons involves a common depletable trans-factor, a chimeric gene containing the ndhD editing site was expressed in tobacco plastids. The data show that, as for psbL, editing of the ndhD site requires a depletable trans-factor. However, this trans-factor is distinct from that required for psbL editing.

In maize plastids, the translation initiation codon of rpl2 is created by editing (Hoch et al., 1991). To test, whether the ACG codon in the maize rpl2 context is edited in tobacco plastids, a Δrpl2/kan gene was constructed by translationally fusing the N-terminal segment of rpl2 with the kan coding region. The chimeric mRNA is not edited in tobacco, but provides a useful selectable marker in cereals such as maize and rice.

The following examples are provided to merely illustrate typical protocols for carrying out the instant invention. They are not intended to limit the scope of the invention in any way.

EXAMPLE I

Editing-based Ekan and Eaada Selectable Marker Genes

A. Construction of the Chimeric Genes

Figure 2A:
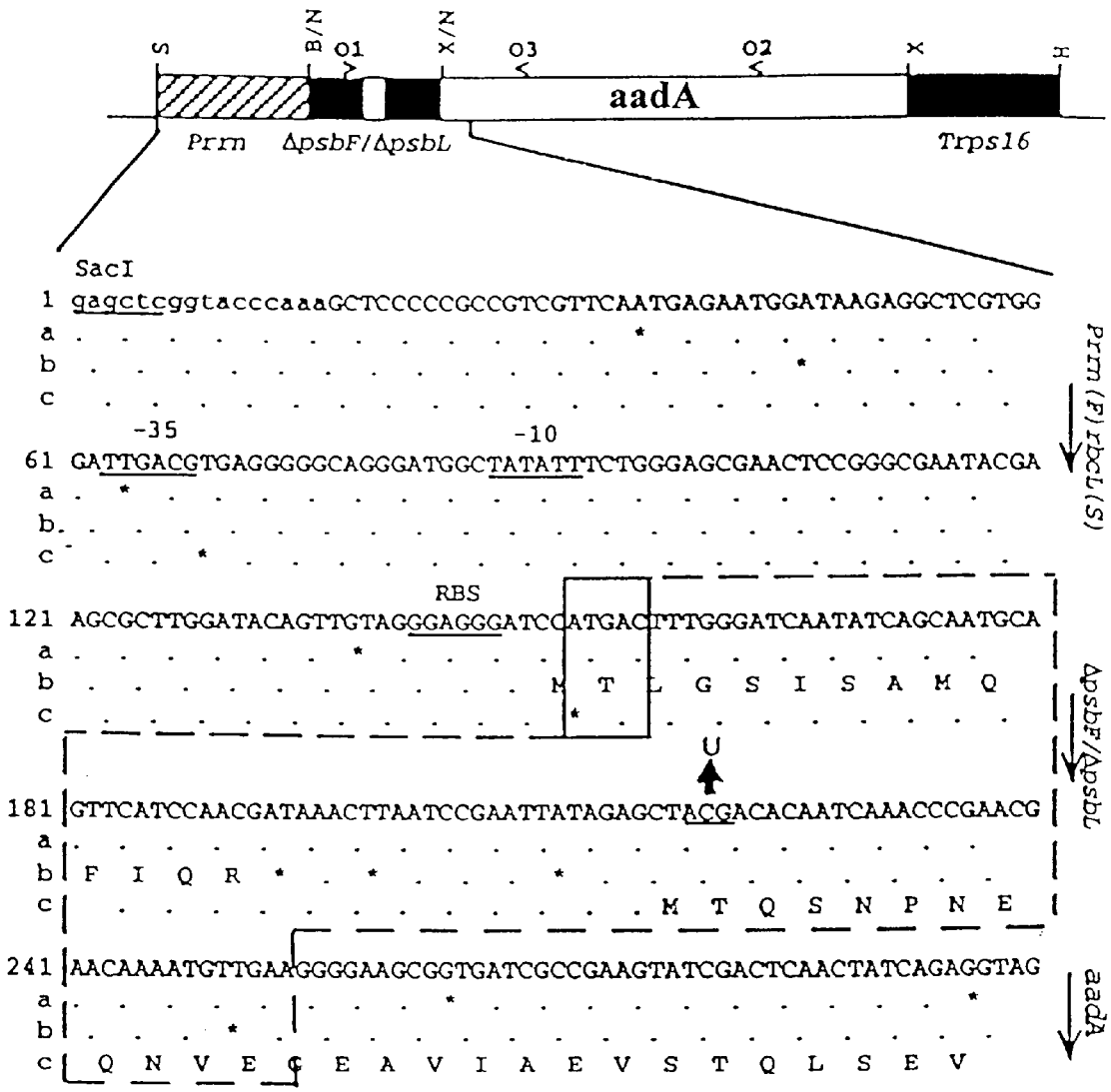
FIGS. 2A and 2B are a physical map and partial DNA sequence (SEQ ID NOS: 4 and 7) showing, the EaadA gene in plasmid pJLM20, FIG. 2A, and the Ekan gene in plasmid pJLM18 in FIG. 2B. The conserved −10/−35 promoter elements and ribosome binding site (RBS) are underlined in the Prrn sequence. DNA sequence derived from the ΔpsbF/ΔpsbL region is bounded by dashed lines, new sequence introduced during construction is in the solid box. The edited psbL initiation codon (from ACG to AUG) is underlined. Trps16 is the 3'-untranslated region of the plastid rps16 ribosomal protein gene. The positions for oligonucleotides O1, O2 and O3 (SEQ ID NOS: 17, 18 and 19) in EaadA, and for O1, O4 and O5 (SEQ ID NOS: 17, 20 and 21) in Ekan are indicated. Abbreviation of restriction sites: B, BspHI; H, HindIII; N, NcoI; S, SacI; X, XbaI.

The psbL gene encodes a peptide of photosystem II and is part of the psbE operon (Carillo et al., 1986; FIG. 1 above). A 98-nucleotide fragment (SEQ ID NO: 1) spanning the psbL editing site, ΔpsbF/ΔpsbL, was cloned upstream of the spectinomycin resistance gene (aadA) coding sequence such that the N-terminus of psbL was translationally fused with aadA. The ΔpsbF/ΔpsbL fragment (see SEQ ID NO: 1) contains 40 nucleotides of the psbF C-terminus, 22 nucleotides of the intergenic region between psbF and psbL and 36 nucleotides of the psbL N-terminus. The construct was cloned in the Prrn/Trps16 plastid expression cassette (FIG. 2A). Prrn contains the plastid rRNA operon promoter, a ribosome binding site and a translational initiation codon (ATG). In the chimeric construct (SEQ ID NO: 4), the truncated psbF coding region forms an open reading frame with the Prrn initiation codon (ATG), whereas the translation of the EaadA reading frame (psbL-aadA fusion peptide) is dependent on the creation of a translation initiation codon (AUG from ACG) by editing the psbL site. Note that the two coding regions are in different reading frames in the EaadA mRNA. See FIG. 2A.

Figure 2B:
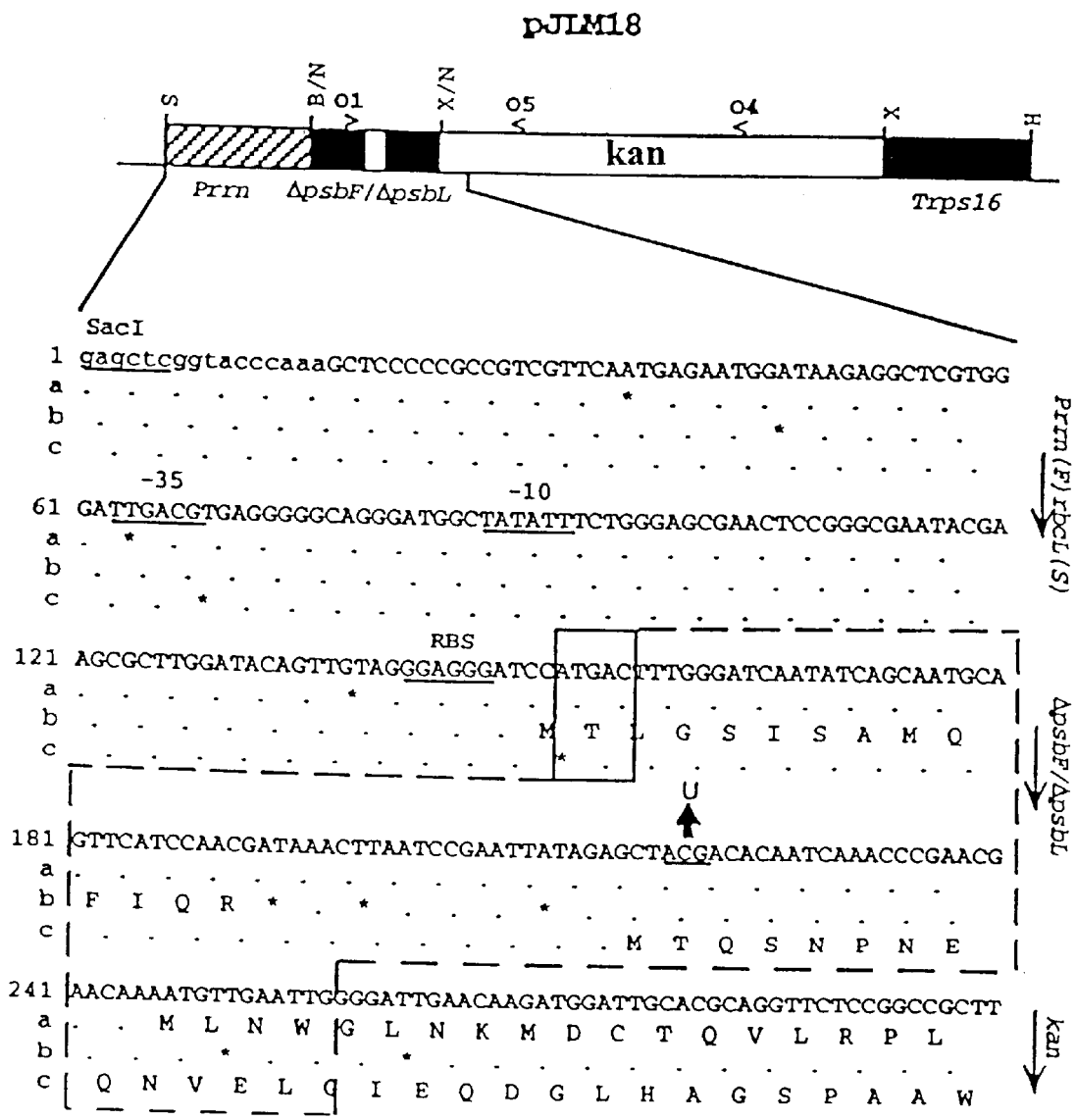

The Ekan gene was obtained by translationally fusing psbL with kan, a kanamycin resistance gene encoding neomycin phosphotransferase using the same ΔpsbF/ΔpsbL fragment, shown in FIG. 2B see SEQ ID NO: 7. Ekan is similar to the EaadA gene, except that it has 39 nucleotides instead of 36 nucleotides of the psbL N-terminus (SEQ ID NO: 7). A detailed technical description of the gene construction is set forth below.

The Ekan gene, shown in FIG. 2B, in plasmid pJLM18 was constructed in a pBluescript KS+ plasmid (Stratagene). The Ekan coding region in pJLM18 is expressed in the Prrn/Trps16 cassette. The Prrn 5'-regulatory region consists of the plastid rRNA operon promoter and a ribosome binding site and is on an EcoRI/NcoI fragment. Prrn derives from plasmid pZS195, the progenitor of plasmid pZS197 (Svab and Maliga, 1993) in which the translational initiation codon (ATG) is included in the NcoI site. The NcoI site of Prrn was ligated to the BspHI site of a BspHI/XbaI fragment; the NcoI/BspHI fusion eliminated both restriction sites. The BspHI/XbaI oligonucleotide was obtained by annealing the overlapping 5'CATTCATGACTTTGGGATCAATATCAG-CATATGCA GTTCATCCAACGATAAACTTAATC-CGAATTATAG AGC-3' (SEQ ID NO: 15) and 5'CGGTCTGAATTCAAT-TCAACATTTTGTTCGTTCGGGTTTGATTGTGTCGTA GCTCTATAATTCGGATTAAG-3' (SEQ ID NO: 16) single-stranded oligonucleotides and extension with the Klenow fragment of DNA polymerase I. The BspHI/XbaI fragment contains the sequence framed in FIG. 2B (SEQ ID NO: 7), including the ΔpsbF/ΔpsbL sequence encoding the C-terminal end of psbF, the intergenic region and the N-terminal portion of psbL. As the result of the NcoI/BspHI fusion, the C-terminal end of psbF is translated from the Prrn translational initiation codon (ATG). To translationally fuse the 14 N-terminal codons of psbL with the kan coding region, the XbaI single-stranded overhang of the BspHI/XbaI fragment and the single-stranded overhang of the NcoI site of kan (including the translational initiation codon) was removed by mung bean nuclease treatment, and subsequently ligated. The kan coding region derives from plasmid pTNH4 as an NcoI/XbaI-fragment (Carrer et al., 1993). The Trps16 fragment is contained within an XbaI/HindIII fragment, and was linked to the Ekan coding region via the XbaI site. The Trps16 fragment contains the rps16 gene 3'-regulatory region between nucleotides 5,087 to 4,939 in the ptDNA (Shinozaki et al., 1986). The XbaI-site at the 5'-end of the fragment was created by oligonucleotide-directed mutagenesis; the 3'-end of the fragment was excised from the plastid genome at an EcoRI-site at nucleotide position 4,938. (Staub and Maliga, 1994). The EcoRI-site was subsequently converted to a HindIII-site by linker-ligation. For introduction into the plastid genome, the Ekan construct was cloned as an EcoRI/HindIII fragment in the multiple cloning site of plastid vector pPRV111B (Zoubenko et al., 1994; Gene Bank Accession No. U12813), which is adjacent to a selectable aadA gene.

The EaadA gene shown in FIG. 2A, in plasmid pJLM20 was constructed in a pBluescript KS+ plasmid as described for the Ekan gene. The NcoI/XbaI fragment containing the aadA coding region is derived from plasmid pHC1 (Carrer et al., 1991) and the aadA coding region is translationally fused with the 12 N-terminal codons of the tobacco psbL gene. For introduction into the plastid genome, the EaadA gene was cloned in plastid insertion vector pPRV100B (Zoubenko et al., 1994, Gene Bank Accession No. U12811). The pPRV100B vector carries a multiple cloning site flanked by ptDNA sequences, but no selectable plastid marker gene.

While kanamycin, spectinomycin and/or streptomycin resistance is exemplified herein, the use of other selectable marker genes is contemplated. A list of such genes is set forth in Table I below (Potrykus et al., (1995) in *Gene Transfer to Plants,* Springer Verlag.

TABLE I

Selectable marker genes for plant transformation

| Selective agent | Marker gene | Gene Product |
|---|---|---|
| Kanamycin, G418 | nptII | Neomycin; Phosphotransferase II |
| Gentamycin | aacC3 aacC4 | Gentamycin-3-N-acetyltransferase |
| Hygromycin | hph, hpt | Hygromycin phosphotransferase |
| Methotrexate | dhfr | Dihydrofolate reductase |
| Spectinomycin | 16S rDNA | 16S rRNA |
|  | aadA | Aminoglycoside-3'-adenyltransferase |
| Streptomycin | SPT | Streptomycin phosphotransferase |
|  | 16S rDNA | 16S rRNA |
|  | aadA | Aminoglycoside-3'-adenyltransferase |
| Bleomycin Phleomycin | ble |  |
| Blasticidin | bsr | Blasticidin S deaminase |
| Sulfonamide | sul | Dihydropteroate synthase |
| Phosphinothricin | bar | Phosphinothricin acetyltransferase |
| Chlorsulfuron | als csr-1 | Acetolactate synthase |
| Bromoxynil | bxn | Bromoxynil nitrilase |
| Glyphosate | EPSPS | 5-enolpyruvyl-shikimate-3-phosphate synthase |
| 2,4-D | tfdA | 2,4-dichlorophenoxyacetate monooxygenase |
| Atrazine | psbA | $Q_B$ protein |
| 2,2-DCPA |  | Dehalogenase |
| 4-methyl-tryptophane | tdc | Tryptophane decarboxylase |
| Nitrate | NR | Nitrate reductase |
| S-aminoethyl-L-cysteine | DHPS | Dihydropicolinate synthase |
| lysine/threonine | AK | Aspartate kinase |
| aminoethyl-cysteine | osc | Octopine synthase |

B. Transformation and Selection of Antibiotic Resistant Transplastomic Lines

The EaadA gene was cloned into the plastid transformation vector pPRV100B (Zoubenko et al., 1994) to yield plasmid pHC94 which was introduced into tobacco chloroplasts by the biolistic process. The chimeric gene integrated into the plastid genome via two homologous recombination events in the trnV-rps7/12 intergenic region. In a sample of 50 bombarded leaves, selection for spectinomycin resistance resulted in the isolation of 43 spectinomycin resistant clones. Out of these, 34 were confirmed to carry the EaadA gene by DNA gel blot analysis (data not shown). Expression of antibiotic resistance indicated editing of the chimeric EaadA. The efficiency of selection for the EaadA gene, approximately one plastid transformant per bombarded leaf sample, was comparable to the efficiency of selection for an aadA gene whose expression was independent of editing (Svab and Maliga, 1993). Three independently transformed lines, Nt-pHC94-1, Nt-pHC94-10 and Nt-pHC94-11, were further studied. As direct selection for kanamycin resistance is inefficient (Carrer et al., 1993), the Ekan gene was linked to a spectinomycin resistance gene in transformation vector pPRV111B to yield plasmid pJLM23. Direct selection of plastid transformants was attempted after bombardment with pJLM23-plasmid coated tungsten particles. No kanamycin resistant clones were obtained in a sample of 200 bombarded leaves (100 each selected on 50 µg/ml and 100 µg/ml kanamycin sulfate). However, transgenic plants containing the Ekan gene were obtained by selection for the linked spectinomycin-resistance gene. Three independently transformed lines, Nt-pJLM23-2, Nt-pJLM23-14 and Nt-pJLM23-18, were further studied. Leaf segments from each of the clones proliferated on kanamycin medium (50 µg/ml) indicating phenotypic expression of the Ekan gene. The methods used for plastid transformation are described in greater detail below.

Tobacco (*Nicotiana tabacum* cv. Petit Havana) plants were grown aseptically on agar-solidified medium containing MS salts (Murashige and Skoog, 1962) and sucrose (30 g/l). Leaves were placed abaxial side up on RMOP media for bombardment. The RMOP medium consists of MS salts, N6-benzyladenine (1 mg/l), 1-naphthaleneacetic acid (0.1 mg/l), thiamine (1 mg/l), inositol (100 mg/l), agar (6 g/l) at pH 5.8, and sucrose (30 g/l). The DNA was introduced into chloroplasts on the surface of 1 µm tungsten particles using the DuPont PDS100He Biolistic gun (Maliga, 1995). Spectinomycin resistant clones were selected on RMOP medium containing 500 µg/ml of spectinomycin dihydrochloride. Resistant shoots were regenerated on the same selective medium, and rooted on MS agar medium (Svab and Maliga, 1993). Kanamycin resistant clones were selected on RMOP medium containing 50 or 100 µg/ml kanamycin sulfate (Carrer et al., 1993).

C. Editing of EaadA, Ekan and psbL Transcripts.

Figure 3A:
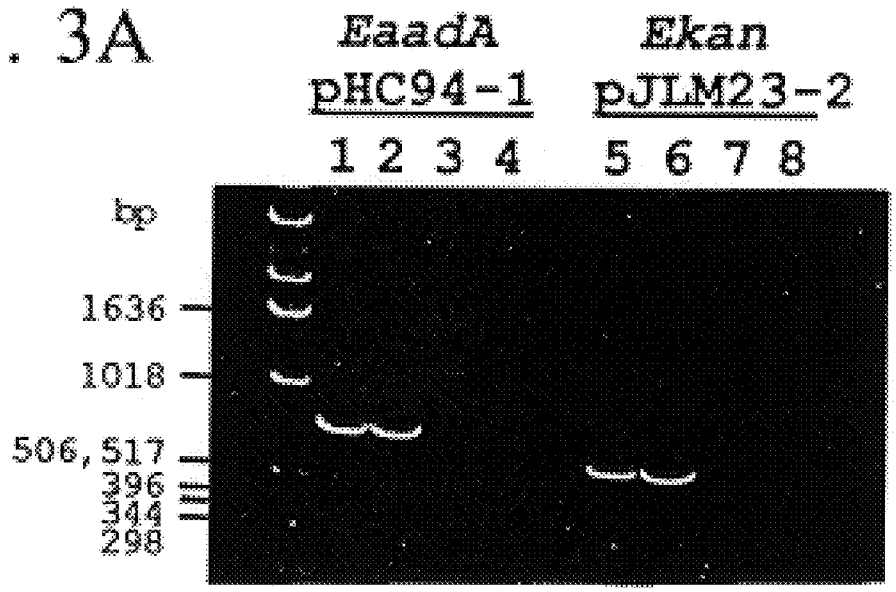
FIGS. 3A, 3B and 3C show a gel and an autoradiogram illustrating editing of the EaadA mRNA in the Nt-pHC94-1 plant, and of the Ekan mRNA in the Nt-pJLM23-2 plant.
Figure 3B:
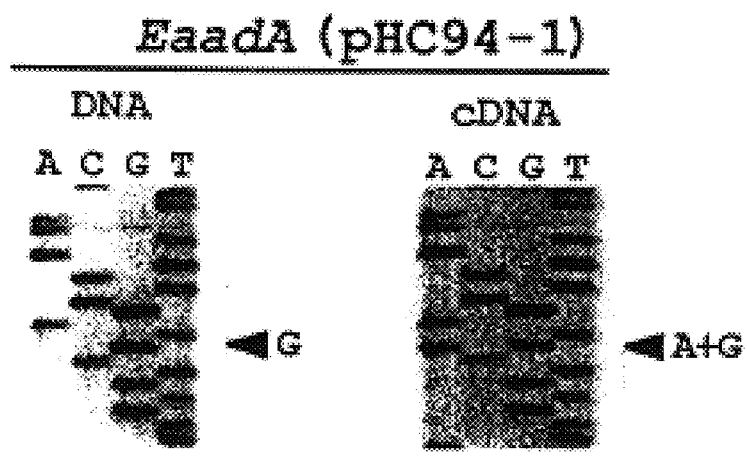

The phenotypic expression of antibiotic-resistance by EaadA and Ekan plants indicated that the chimeric genes were edited since their translation was made dependent on the editing of an ACG to an AUG initiation codon. To directly test for editing of EaadA and Ekan mRNAs, cDNAs were PCR-amplified with primer O1 (SEQ ID NO: 17) within the psbF coding region and primers 02 and 04 (SEQ ID NOS: 18 and 20) within the EaadA and Ekan coding sequences, respectively. The position of the primers is shown in FIG. 2. The PCR amplification products are shown in FIG. 3A. Direct sequencing of the PCR products from three independently transformed EaadA lines and phosphorimager analysis indicated that approximately 70% of the EaadA transcripts are edited. See FIG. 3B and Table II.

TABLE II

| | Unedited mRNAs (%) in the wild-type and transgenic leaves | | | |
|---|---|---|---|---|
| Plant Line | Sample | psbL | EaadA | Ekan |
| Nt-wt | 1 | <0.1 | | |
|  | 2 | 0.7 | | |
|  | 3 | 0.3 | | |
| Nt-pJLM23-2 | 1 | 8.8 | | 30.3 |
| Nt-pJLM23-14 | 1 | 9.2 | | 28.2 |
| Nt-pJLM23-18 | 1 | 10.2 | | 28.4 |
| Nt-pHC94-1 | 1 | 9.5 | 28.7 | |
| Nt-pHC94-10 | 1 | 9.0 | 30.4 | |
| Nt-pHC94-11 | 1 | 10.4 | 29.9 | |

Radioactivity in bands in FIG. 3 corresponding to nucleotides was determined by phosphorimager analysis. The vaLues were normalized for DNA loading and labeling efficiency against six other bands in the same lanes. Percent unedited mRNA = [corrected unedited signal/(corrected edited + corrected unedited signal)] × 100.

Figure 3C:
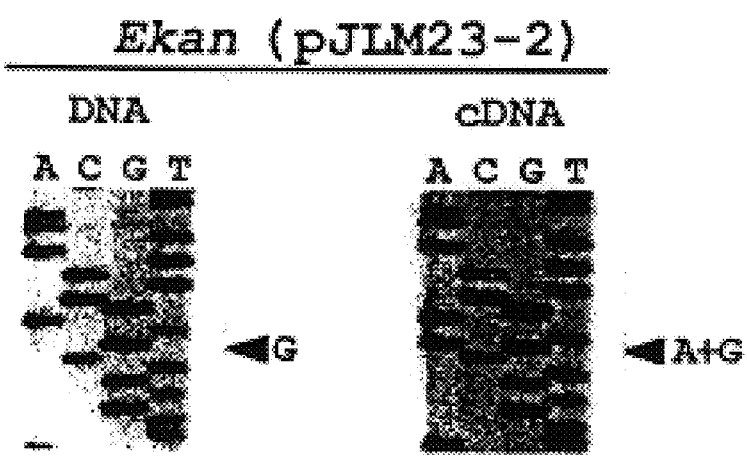
Figure 4A:
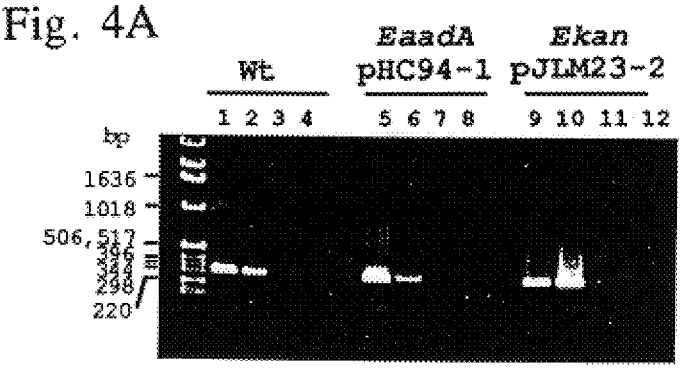
FIGS. 4A, 4B, 4C and 4D depict a gel and autoradiograms illustrating editing of the psbL mRNA in the transgenic plants.
Figure 4B:
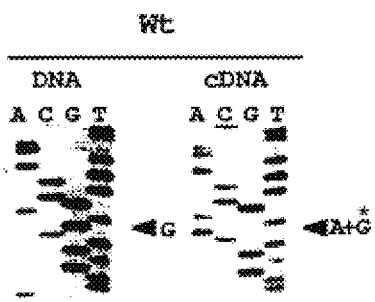
Figure 4C:
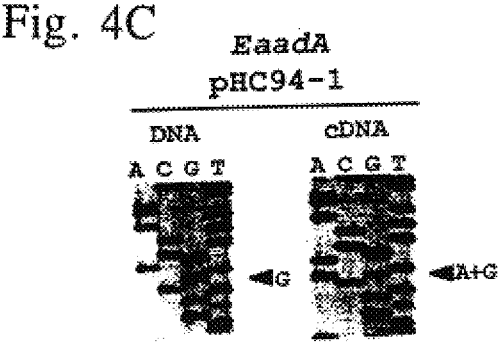
Figure 4D:
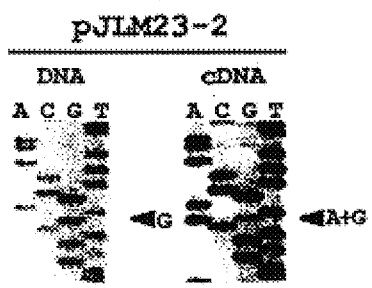

A similar extent of editing was found for the Ekan mRNAs as shown in FIG. 3C and Table II. The partial editing was not due to the presence of contaminating DNA in the RNA samples since no PCR-amplified products were obtained from non-reverse transcribed DNase I-treated RNA samples. See FIG. 3A; lanes 3 and 7. The psbL site in the chimeric transcripts was only partially (approximately 70%) edited while in leaves of wild-type plants the psbL mRNA is >99% edited (Kudla et al., 1992; Bock et al., 1993). Therefore it was of interest to determine whether or not the editing of the psbL mRNA is affected in the transgenic plants. The psbL cDNAs were PCR-amplified with primers O1 and O6 (SEQ ID NOS: 17 and 22 respectively) within the psbF and psbJ coding regions as shown in FIG. 1A, from wild type and transgenic plants. Direct sequencing of the PCR products revealed that the transgenic plants contained approximately 10% unedited psbL mRNA. This indicates a >10-fold increase in the level of unedited psbL mRNA in the transgenic plants. See FIGS. 4A, 4B, 4C, 4D and Table II. Artifacts due to DNA contamination of RNA samples were excluded by the lack of PCR products from non-reverse transcribed DNase I-treated RNA samples. See FIG. 4A, lanes 3, 7 and 11. Methods utilized to study the editing in plastid mRNAs are set forth below.

Total cellular DNA was isolated according to Mettler (1987). Total cellular RNA was extracted using TRIzol (Gibco BRL). Reverse transcription of proteinase K- and DNAse I-treated RNA samples were carried out as described by Kudla et al.(1992). DNA and cDNA were amplified by PCR according to standard protocols: 1 min at 92° C., 2 min at 55° C., 1.5 min at 72° C., 30 cycles.

The PCR amplification products were separated in 1.5% agarose gels and purified using the Geneclean II kit (BIO 101 Inc.). Direct sequencing of DNA was performed as described (Bachmann et al., 1990) using the Sequenase kit (USB) and the detergent Nonidet P-40.

The following is a list of primers used for PCR.

O1 5'-CAATATCAGCAATGCAGTTCATCC-3' (SEQ ID NO: 17)
O2 5'-CCAAGCGATCTTCTTCTTGTCCAA-3' (SEQ ID NO: 18)
O3 5'-GCGCTCGATGACGCCAAC-3' (SEQ ID NO: 19)
O4 5'-GCGCTCGATGACGCCAAC-3' (SEQ ID NO: 20)
O5 5'-CACGACGAGATCCTCGCCG-3' (SEQ ID NO: 21)
O6 5'-GGAATCCTTCCAGTAGTATCGGCC-3'(SEQ ID NO: 22)
O7 5'-GGAAAATAAAACAGCAAGTAC-3' (SEQ ID NO: 23)
O8 5'-CAAATATTGCAAAGTCCCGG-3' (SEQ ID NO: 24)
O9 5'-CCGGATCGCCACCTACAC-3' (SEQ ID NO: 25)
O10 5'-TGGCTATAACAGAGTTTCTC-3' (SEQ ID NO: 26)
O11 5'-GGATTTCCAGAAGAAGATGCC-3' (SEQ ID NO: 27)
O14 5'-GTTCGTTCGGGTTTGATTGTG-3' (SEQ ID NO: 28)
O15 5'-GAACTCAACGGGCCCTTCCCC-3' (SEQ ID NO: 29)
O16 5'-GGAGGGAAGTGGAGTAAATGGCCG-3' (SEQ ID NO: 30)

D. Relative Abundance of psbL, EaadA and Ekan mRNAs

Figure 5A:
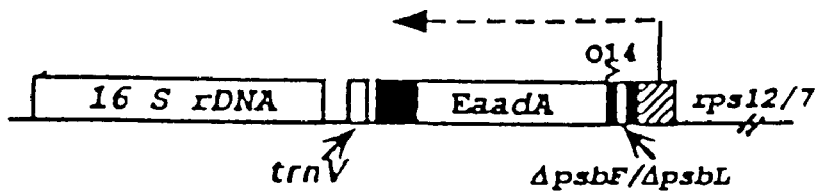
FIGS. 5A and 5B show a partial DNA map of the plastid genome and an autoradiogram depicting the steady-state levels of psbL and chimeric mRNAs.
Figure 5A:
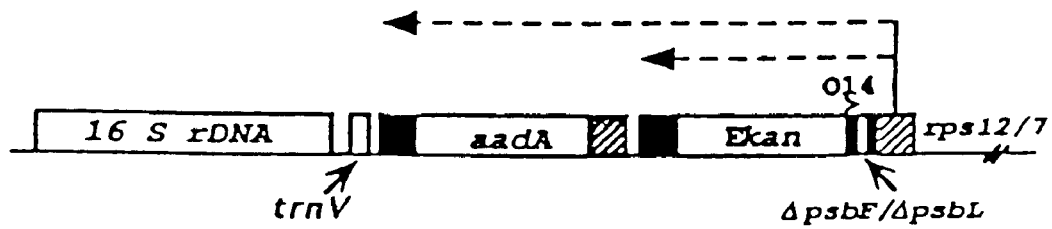
Figure 5B:
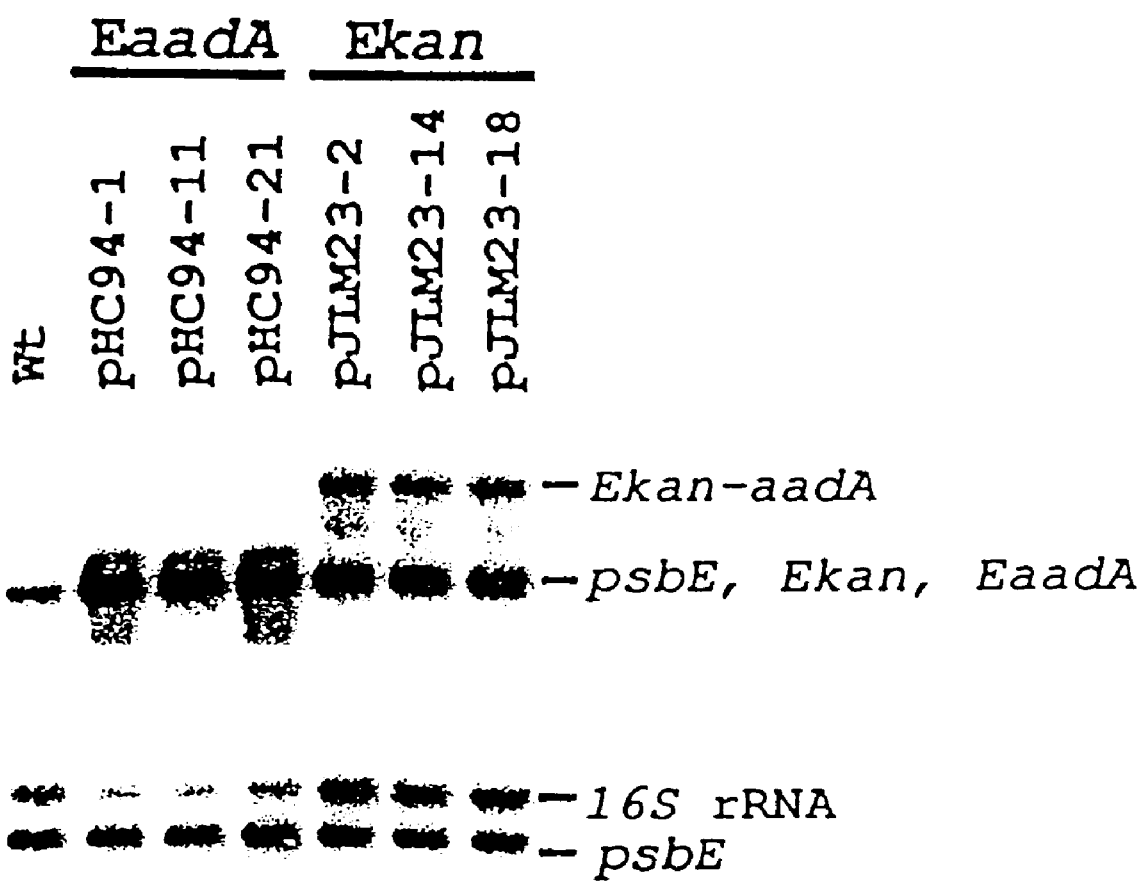

Accumulation of partially edited psbL mRNA in the transgenic lines could be due to its competition with the chimeric EaadA or Ekan mRNAs for a limiting common factor(s) that is required for editing. Therefore, the relative abundance of the psbL and chimeric transcripts was determined. It should be noted that both the polycistronic psbE (Carillo et al., 1986) and the EaadA and Ekan mRNAs are approximately 1.1-kb in size. To quantify the accumulation of these transcripts, differential DNA probes on Northern blots were utilized. See FIGS. 5A and 5B Probing with the psbJ coding sequence fragment indicated that the 1.1-kb psbE operon mRNA, which contains the psbJ and psbL reading frames, accumulates to a similar extent in the wild-type and transformed plants. See FIG. 5B, lower panel. The O14 oligonucleotide probe (SEQ ID NO: 28) hybridizes to the mRNA containing the ΔpsbF/ΔpsbL region present in both the psbE operon and the chimeric EaadA and Ekan transcripts. The O14 probe (SEQ ID NO: 28) detected about 4× more RNA in the transgenic plants indicating a 1:3 ratio of the polycistronic psbE to chimeric mRNAs. See FIG. 5B, upper panel. Procedures used for RNA gel analysis are discussed below.

Total RNA was extracted using TRIzol (Gibco BRL). RNA was electrophoresed in formamide-containing 1% agarose gel and transferred to nylon membrane (Amersham). Hybridization to $^{32}$P-end-labeled oligonucleotide probe O14 (SEQ ID NO: 28) was carried out in 6×SSPE, 0.5% SDS, 10× Dendardt's solution, 100 mg/ml tRNA, 0.1% Sodium Pyrophosphate at 45° C. Hybridization to random primed (Boehringer Mannheim) $^{32}$P-labeled DNA fragment probes was carried out at 65° C. in rapid hybridization buffer (Amersham). RNA levels in samples that hybridized to the probes were quantitated by PhosphorImager analysis (Molecular Dynamics).

E. Editing of Other mRNAs is Not Affected in the Transgenic Plants.

Increased demand for psbL editing in the transgenic plants led to a reduction in its editing efficiency. Experiments were performed to determine if editing of other mRNAs is also affected in the transgenic plants. Two sites were tested in the rpoB, and two in the ndhB transcripts. See Table III.

TABLE III

List of tested editing sites in wild-type and transgenic plants

| | Codon no. | | Codon (amino acid) | |
|---|---|---|---|---|
| Editing site | Maize | Tobacco | Unedited | Edited |
| rpoB site I[a] | 156 | 158 | TCG (Ser) → | TTG (Leu)[c] |
| rpoB site II[b] | 182 | 184 | TCA (Ser) → | TTA (Leu) |
| ndhB site I[b] | 156 | 156 | CCA (Pro) → | CTA (Leu) |
| ndhB site II[b] | 196 | 196 | CAT (His) → | TAT (Tyr) |

[a]Reference: Zeltz et al., 1993
[b]Reference: Maier et al., 1992
[c]In tobacco, a TCA codon is edited to a TTA codon.

Figure 6:
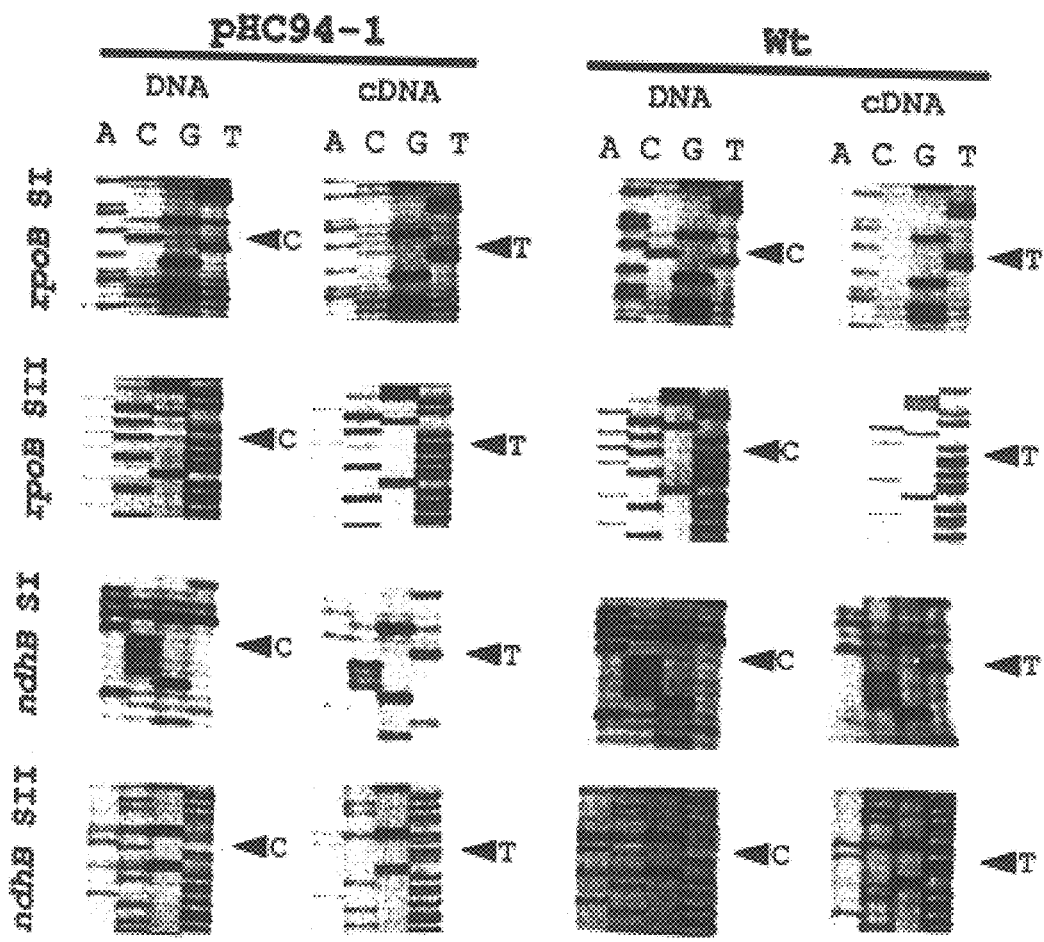
FIG. 6 is a series of autoradiograms illustrating editing of the rpoB and the ndhB transcripts in the wild-type and transgenic Nt-pHC94-1 plants. The DNA and cDNA sequences corresponding to each gene were PCR amplified using the following primers: O8 and O9 (SEQ ID NOS: 24 and 25) for rpoB; O10 and O11 (SEQ ID NOS: 26 and 27) for ndhB. The sequencing primer for rpoB was O8 (SEQ ID NO: 24), for ndhB was O1 (SEQ ID NO: 17). The editing site in the sequence is marked by an arrowhead. Arrowhead points at C in DNA which is edited to T at sites I and II of the rpoB and ndhB transcripts.

The rpoB and ndhB editing sites were originally reported for maize, and confirmed for tobacco in this study. Editing sites I and II of rpoB are almost fully edited in wild-type tobacco, shown in FIG. 6, as has been observed for maize and barley (Zeltz et al., 1993). Similarly, sites I and II of the ndhB transcript are fully edited in wild type tobacco also shown in FIG. 6, as reported for maize (Maier et al., 1992). The editing efficiency for the same sites was tested in three lines each of the EaadA- and Ekan-expressing plants. No significant difference in the editing efficiency between wild-type and transformed plants was found for any of the four sites. Data in FIG. 6 are shown for a Nt-pHC94-1 plant, one of the EaadA-expressing lines. Lack of change in the editing efficiency at any of the sites other than psbL indicates that expression of the chimeric genes specifically compromises the editing efficiency of the psbL site.

Discussion

The above described examples are the first demonstration of the editing of chimeric mRNAs in plastids. Editing of both EaadA and Ekan transcripts indicates that 98 and 101 nucleotides, respectively, of the ΔpsbF/ΔpsbL fragment (SEQ ID NO: 1) are sufficient to direct editing at the psbL site. Accumulation of EaadA or Ekan mRNA at levels approximately 3-fold above that of the psbE polycistronic message containing the psbL reading frame led to a significant (>10-fold) increase in the level of unedited psbL transcript. Increase in the level of unedited psbL mRNA from <1% to approximately 10% did not have any deleterious consequence that could have been detected at the phenotypic level. The chimeric mRNAs were also partially edited in the transgenic plants.

Partial editing of both psbL and chimeric mRNAs suggests depletion of a limiting trans-acting factor(s) that is required for editing of the shared site. However, the editing efficiency of four other sites was unaffected suggesting that the depleted factor is specifically required for editing of the psbL transcript and is not a component of the general editing machinery. It is therefore conceivable that each of the editing sites in the chloroplast genome requires some factors for editing that are unique to them. This conclusion is reinforced by the lack of any obvious sequence motif common to the 98 nucleotide ΔpsbF/ΔpsbL fragment (SEQ ID NO: 1) and sequences surrounding the other four tested editing sites. Therefore, it appears likely that the editing of these sites is directed by sequences and factors that are unique to each.

As an alternative to depletion of a site-specific factor, existence of "strong" and "weak" editing sites was also considered. Accordingly, the psbL site would be weak and its editing frequency would be lowered by the presence of excess chimeric RNA competing for a limiting but common editing factor, whereas the others would be strong sites that remain unaffected. This explanation is considered unlikely based on other data in the literature which are consistent with the existence of site-specific editing factors in plastids. The psbF mRNA is edited in spinach plastids by a C to U conversion, changing a serine to a conserved phenylalanine codon. In tobacco at this position a phenylalanine codon is already present at the DNA level. When the tobacco psbF gene was modified to match the spinach sequence, the heterologous editing site was unedited, although the adjacent psbL site is edited in both species (Bock et al., 1994). It appears therefore that tobacco lacks the capacity to edit the spinach psbF mRNA while maintaining the capacity to edit the psbL site which is common to both species. Another case consistent with site-specific editing is site IV of the rpoB mRNA which is edited in maize but not in barley, although the sequences surrounding the site are highly conserved. Interestingly, the editing of three other sites in the same transcript is conserved between the two species (Zeltz et al., 1993). These observations suggest that the editing capacity of an individual site may be lacking without affecting the editing capacity of other sites, supporting site-specific editing in plastids.

EXAMPLE II

Editing Based ΔpsbL/kan and ΔndhD/kan Selectable Marker Genes

In plastids, editing of an ACG codon to an AUG codon creates the translation initiation codon for the psbl and ndhD transcripts in tobacco. To identify the RNA segment required for psbL editing, chimeric kanamycin resistance genes were constructed containing psbL deletion derivatives, and tested in vivo for editing in transgenic plants. The data demonstrate that a 22 nucleotide segment (SEQ ID NO: 10) is sufficient to direct efficient psbL editing, including 16 nucleotides upstream and 5 nucleotides downstream of the editing site. Mutation of the A nucleotide to a C upstream of the editing site completely abolished editing, while mutation of the downstream G to a C only reduced the editing efficiency. Out of the 22 nt editing target sequence (SEQ ID NO: 10), the 16 upstream nucleotides were found to compete with the endogenous psbL transcript for a depletable trans-factor. To test whether editing of initiation codons involves a common trans-factor, a chimeric gene containing the ndhD editing site was expressed in tobacco plastids. As for psbL, editing of the ndhD site requires a depletable trans-factor. However, the ndhD trans-factor is distinct from that required for psbL editing. Distinct cis-sequences and trans-factor requirements for the psbL and ndhD editing sites indicates an individual recognition mechanism for the editing of plastid initiation codons.

A. Defining the cis-sequences Directing psbL Editing

As mentioned previously, the psbL gene is part of the psbE operon which contains the psbE, psbF, psbL and psbJ reading frames (Carillo et al., 1986). In the earlier examples (Chaudhuri et al., 1995) the editing of the psbL translation initiation site in a chimeric mRNA containing a 98 nt ΔpsbF/ΔpsbL fragment (SEQ ID NO: 1) was described (−63/+34 in plasmid pSC2, FIG. 7A). In the chimeric construct of FIG. 7A, the first open reading frame is a truncated psbF (ΔpsbF) gene containing 40 nt of the C-terminus. The second open reading frame contained 36 nt of the N-terminus of psbL (ΔpsbL) translationally fused with the bacterial kanamycin resistance (kan) gene to yield the ΔpsbL/kan fusion protein. The two open reading frames are separated by 22 nt of intergenic region. See FIG. 7A.

To identify the sequences required for psbL editing, deletion derivatives of the 98 nt ΔpsbF/ΔpsbL fragment (SEQ ID NO: 1) were tested for editing in vivo. As before, the psbL deletion derivatives were fused N-terminally to bacterial kanamycin resistance gene (kan), and cloned in the plastid Prrn/Trpsl6 expression cassette to create chimeric genes. See FIG. 7A. Thus, for all the constructs, translation of ΔpsbL/kan was made dependent on editing of the psbL A<u>C</u>G codon to A<u>U</u>G codon. Editing therefore could be tested by the kanamycin resistance phenotype. The only exception is the chimeric gene containing −2/+34 fragment (in plasmid pSC10) where the initiation codon for the translation of ΔpsbL/kan reading frame was provided by Prrn. The psbL deletion derivatives were introduced into the tobacco plastid genome by linkage to a selectable spectinomcyin resistance gene (Chaudhuri et al., 1995).

Figure 7A:
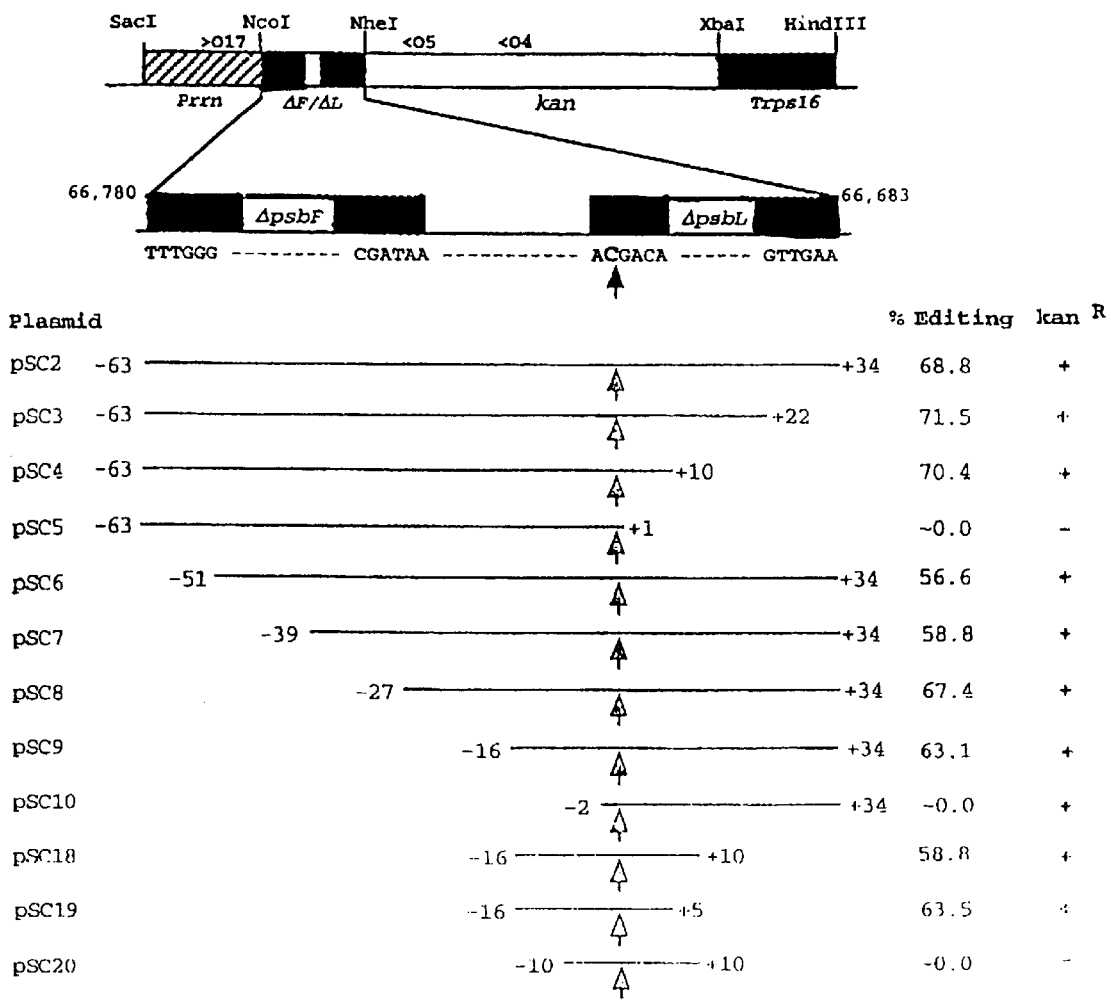
FIGS. 7A and 7B depict a partial map and a series of autoradiograms illustrating the approach by which the region required for psbL editing was defined.
Figure 7B:
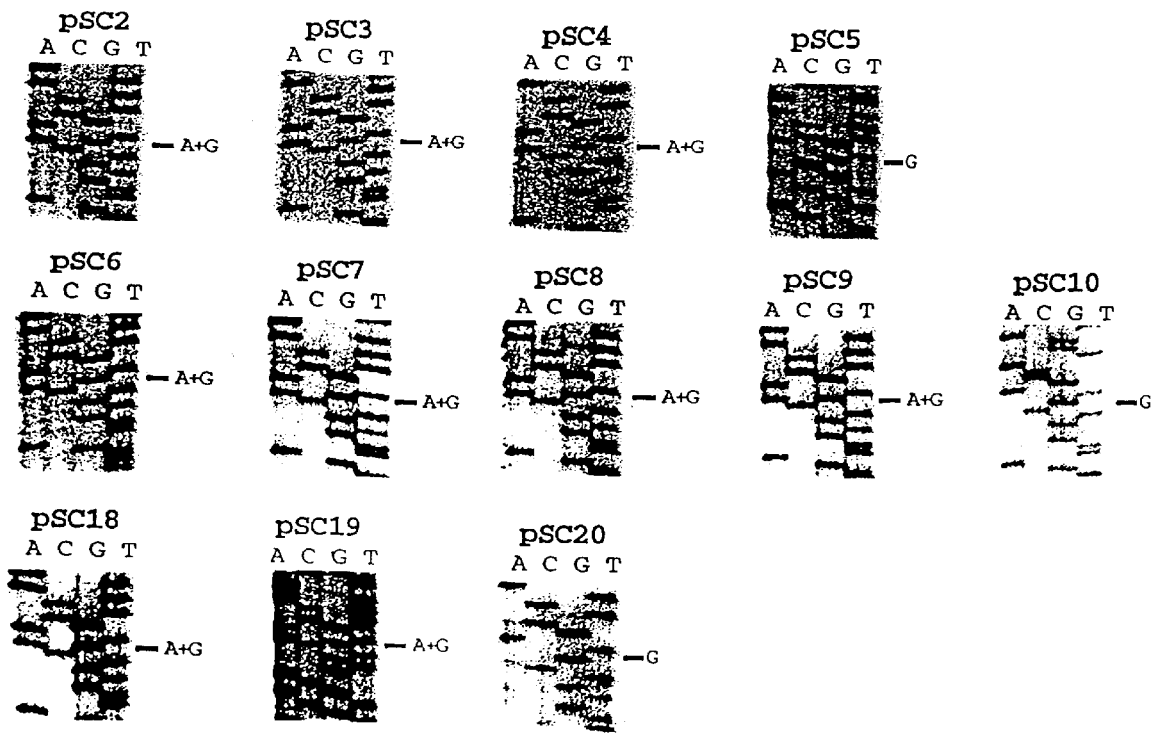

The upstream deletion series included constructs with 5'-ends at positions −63, −51, −39, −27, −16, −10 and −2 nucleotides relative to the editing site (position 0). The downstream deletion series included constructs with 3'-ends at positions +34, +22, +10, +5 and +1 nucleotides relative to the editing site. The editing efficiency of the chimeric mRNAs was determined by direct sequencing and phosphoimager analysis of PCR-amplified cDNAs. Editing in the deletion derivatives was maintained as long as the constructs contained 16 nt of upstream and 5 nt of the downstream sequence relative to the editing site as shown in FIGS. 7A and 7B. Interestingly, in the deletion series, the % of the chimeric mRNA that is edited (editing efficiency) was either similar to that of the full size 98 nt ΔpsbF/ΔpsbL fragment (about 50%–70%); SEQ ID NO: 1, or barely detectable (~0%). Expression of kanamycin resistance was also a reliable qualitative marker of editing in all transformants in which translation of the chimeric mRNA was dependent on editing. See FIG. 7A. The exception were plants obtained by transformation with plasmid pSC10 in which kanamycin resistance is expressed from the translation initiation codon contained in the Prrn promoter fragment. Construction of the deletion derivatives is set forth below.

The psbL deletion derivatives and the ndhD gene fragment were generated by PCR amplification with 5' primers carrying NcoI restriction site and 3' primers carrying NheI restriction site using total cellular DNA from tobacco (cv. Petit Havana). The following primer pairs were used: plasmid pSC2, 023 and 029 (SEQ ID NOS: 37 and 43); plasmid pSC3, 023 and 030 (SEQ ID NOS: 37 and 46); plasmid pSC4, 023 and 031 (SEQ ID NOS: 37 and 45); plasmid pSC5, 023 and 032 (SEQ ID NOS: 37 and 46); plasmid pSC6, 024 and 029 (SEQ ID NOS: 38 and 43); plasmid pSC7, 025 and 029 (SEQ ID NOS: 39 and 43); plasmid pSC8, 026 and 029 (SEQ ID NOS: 38 and 43); plasmid pSC9, 027 and 029 (SEQ ID NOS: 40 and 43 ); plasmid pSC10, 028 and 029 (SEQ ID NOS: 42 and 43); plasmid pSC18, 027 and 031 (SEQ ID NOS: 41 and 45); plasmid pSC19, 027 and 034 (SEQ ID NOS: 41 and 48); plasmid pSC20, 033 and 031 (SEQ ID NOS: 47 and 45); pSC23, 037 and 038 (SEQ ID NOS: 51 and 52). The PCR products were digested with NcoI and NheI restriction enzymes.

To introduce suitable restriction sites at the 5'-end of the kan coding region, kan was PCR amplified from pTNH32 (Carrer et al., 1993) using 5' primer (021); SEQ ID NO: 35 carrying NcoI and NheI restriction sites in tandem and 3' primer (022); SEQ ID NO: 36 carrying XbaI restriction site. The PCR product was cloned in NcoI/XbaI digested pUC120 to generate plasmid pSC1.

The chimeric genes were constructed by N-terminal fusion of PCR amplified sequences from tobacco psbL and ndhD genes (NcoI/NheI fragments) to bacterial kan gene lacking the initiation codon (NheI/XbaI fragments). The chimeric genes were then cloned in NcoI/XbaI digested plasmid pLAA24A (Zoubenko et al., 1994). Plasmid pLAA24 is a derivative of plastid transformation vector pPRV111A, (Gene Bank Accession No. U12812) which has a selectable spectinomycin resistance gene, and a uidA reporter gene in the Prrn/Trps16 expression cassette (Zoubenko et al., 1994). The Prrn 5'-regulatory region consists of the plastid rRNA operon promoter and a ribosome binding site and is on an SacI/NcoI fragment. The Trps16 fragment includes the rps16 gene 3'-regulatory region between nucleotides 5,087 to 4,939 in the ptDNA (Shinozaki et al., 1986) and is contained within an XbaI/HindIII fragment. Digestion of plasmid pLAA24A with NcoI/XbaI restriction enzymes removes the uidA coding region from the expression cassette, which is then replaced with the chimeric constructs, also an NcoI/XbaI fragment.

To construct the chimeric genes of the subsequent examples, the following procedures were used. Plastid transformation and plant regeneration were performed as described in Example I. PCR amplification and DNA sequencing were also performed as described in Example I above. The sequencing gels were subjected to phosphoimager analysis (Molecular Dynamics) for quantitation of editing efficiency. Radioactivity in bands corresponding to nucleotides was determined. The values were normalized for sample loading and labeling efficiency against other bands in the same lanes. mRNA editing efficiency (%)=[corrected edited signal/(corrected edited+corrected unedited signal)]× 100. The primers used were as follows:

01: 5'-CAATATCAGCAATGCAGTTCATCC-3' (SEQ ID NO: 17)
04: 5'-CACGACGAGATCCTCGCCG-3' (SEQ ID NO: 20)
05: 5'-GAATAGCCTCTCCACCCA-3' (SEQ ID NO: 21)
06: 5'-GGAATCCTTCCAGTAGTATCGGCC-3' (SEQ ID NO: 22)
07: 5'-GGAAAATAAAACAGCAAGTAC-3' (SEQ ID NO: 23)
017: 5'-AATTCGAAGCGCTTGGATACAGTTGTAGGGA-3' (SEQ ID NO: 31)
018: 5'-GTAAGAGATGTGAATCCGCCTGT-3' (SEQ ID NO: 32)
019: 5'-GCATAAGTCGTTAGAAGGAG-3' (SEQ ID NO: 33)
020: 5'-GAAGAAAGAAAATTAAGGAACC-3' (SEQ ID NO: 34)
021: 5'-CATGCCATGGCTAGCATTGAACAAGATGG ATTGCACG-3' (SEQ ID NO: 35)
022: 5'-GTACTCTAGACCCGCTCAGAAGAACTCG-3' (SEQ ID NO: 36)
023: 5'-CTAGCCATGGCTTTGGGATCAATATCAGCA ATG-3' (SEQ ID NO: 37)
024: 5'-CTAGCCATGGCATCAGCAATGCAGTTCATCC-3' (SEQ ID NO: 38)
025: 5'-CTAGCCATGGCGTTCATCCAACGATAAAC TTAA-3' (SEQ ID NO: 39
026: 5'-CTAGCCATGGCATAAACTTAATCCGAATTAT AGAG-3' (SEQ ID NO: 40)
027: 5'-CTAGCCATGGCCGAATTATAGAGCTACGACAC-3' (SEQ ID NO: 41)
028: 5'-CTAGCCATGGCTACGACACAATCAAACCCGA-3' (SEQ ID NO: 42)
029: 5'-CTAGCTAGCTTCAACATTTTGTTCGTTCGG-3' (SEQ ID NO: 43)
030: 5'-CTAGCTAGCTTCGTTCGGGTTTGATTGTG-3' (SEQ ID NO: 44)
031: 5'-CTAGCTAGCTGATTGTGTCGTAGCTCTATA-3' (SEQ ID NO: 45)
032: 5'-CTAGCTAGCCGTAGCTCTATAATTCGGATT-3' (SEQ ID NO: 46)
033: 5'-CTAGCCATGGTATAGACCTACGACAC-3' (SEQ ID NO: 47)
034: 5'-CTAGCTAGCAAGTGTCGTAGCTCTATA-3' (SEQ ID NO: 48)
035: 5'-AATTATAGAGCTCCGACACAATC-3' (SEQ ID NO: 49)
036: 5'-AATTATAGAGCTACCACACAATC-3' (SEQ ID NO: 50)
037: 5'-CTAGCCATGGTATTTTGAGCACGGGTTTTT CTGGTCC-3' (SEQ ID NO: 51)
038: 5'-CTAGCTAGCTGGAAAAACTACAATTATTGT TAACC-3' (SEQ ID NO: 52)

B. Mutation of the Nucleotides Flanking the psbL Editing Site.

The edited ACG codon to CCG and ACC in the efficiently edited 98 nt ΔpsbF/ΔpsbL fragment (SEQ ID NO: 1) were altered to address the following issues: (1) Whether the flanking nucleotides are critical for editing. (2) Whether the fidelity of editing the correct C is maintained when one of the flanking nucleotides is changed to a C. (3) Whether translation initiation at this site is required for editing, since changing the ACG codon to CCG and ACC would eliminate the possibility of translation initiation at the edited codon.

Mutation of the upstream nucleotide (ACG to CCG; NtpSC14 line) resulted in the loss of editing (~0%). See FIG.

Figure 8:
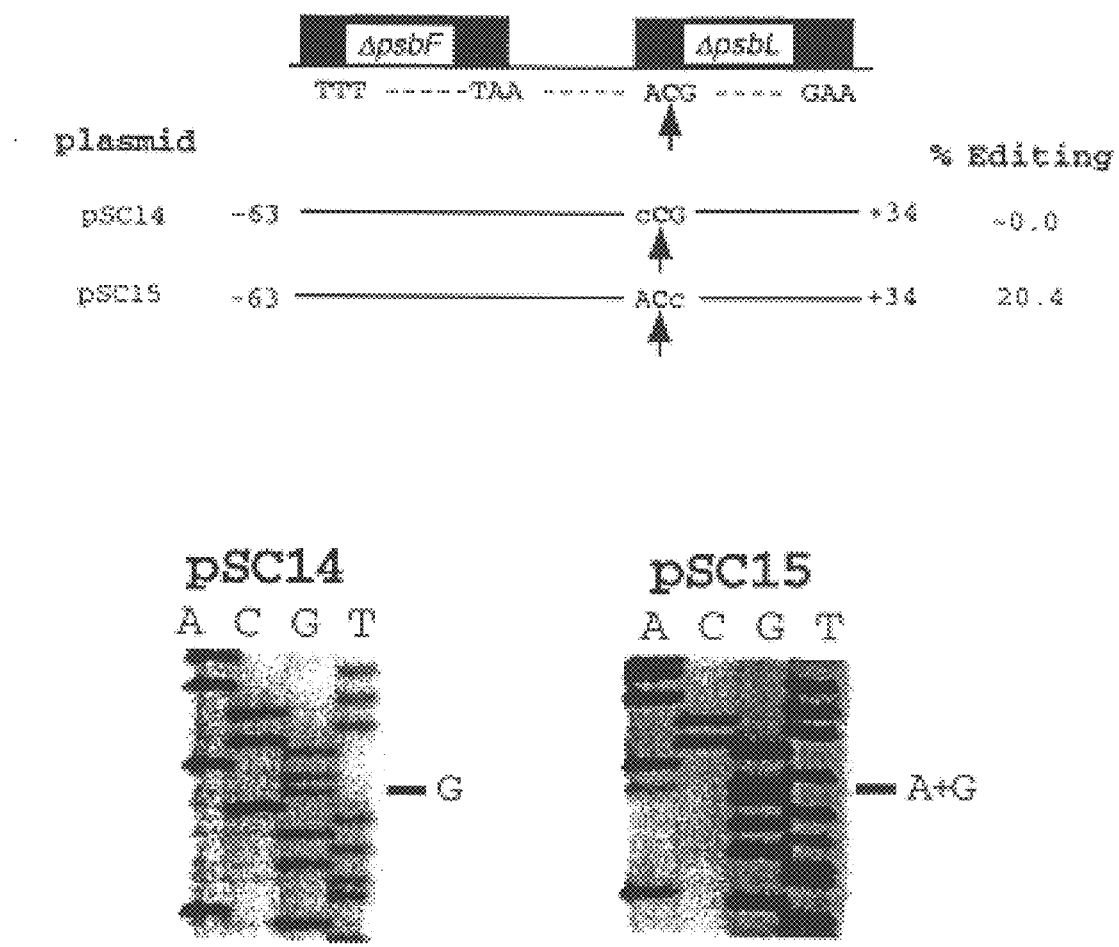
FIG. 8 is a partial DNA map and a pair of autoradiograms illustrating psbL editing in transgenic plants with mutations adjacent to the editing site. The position of the edited C (arrow) and the flanking nucleotides within the 98 nt ΔpsbF/ΔpsbL fragment (SEQ ID NO: 1) are shown in the upper portion of FIG. 8. Mutations in plasmids pSC14 and pSC15 are in lower case. Editing was tested by sequencing the chimeric cDNAs (bottom). Calculated editing efficiencies of the chimeric mRNA (%) are listed. For experimental details see legend to FIGS. 7A and 7B.

8. Mutation of the downstream nucleotide (ACG to ACC; Nt-pSC15 line) allowed editing at the correct C, but at a significantly reduced efficiency, ~20%. See FIG. 8. The mutational analysis therefore indicated that the A residue directly upstream of the edited C is appears to be essential for editing while mutation of the downstream G residue to C is compatible with editing but is required for optimal efficiency. In addition, editing of the correct C in the mutated codon ACC points to a high fidelity mechanism of the editing apparatus in the choice of the editing site. Furthermore, editing of the ACC codon suggests that translation initiation at this codon is not required for editing. Construction of the chimeric genes and introduction into plants was carried out as described in section A for the ΔpsbL/kan derivatives.

The psbL derivatives with a point mutation were obtained by the megaprimer method of PCR (Sarkar and Sommer, 1990) using plasmid pSC2 as the template. These were also designed as NcoI and NheI fragments. The primers used were the following: plasmid pSC14, step I, 035 and 029 (SEQ ID NOS: 49 and 43 respectively), step II, 023 (SEQ ID NO: 37); plasmid pSC15, step I, 036 and 029 (SEQ ID NOS: 50 and 43 respectively), step II, 023 (SEQ ID NO: 37).

C. Identification of psbL mRNA Sequences which Interact with a psbL-specific Editing Factor (psbL-SEF).

In previous examples it has been shown that the editing efficiency of the endogenous psbL transcript is reduced in plastids expressing the chimeric psbL mRNA. Reduced editing efficiency was due to competition of the 98 nt ΔpsbF/ΔpsbL fragment (SEQ ID NO: 1) with the endogenous psbL mRNA for a site-specific editing factor (psbL-SEF) present in limiting amounts (Chaudhuri et al., 1995).

Figure 9A:
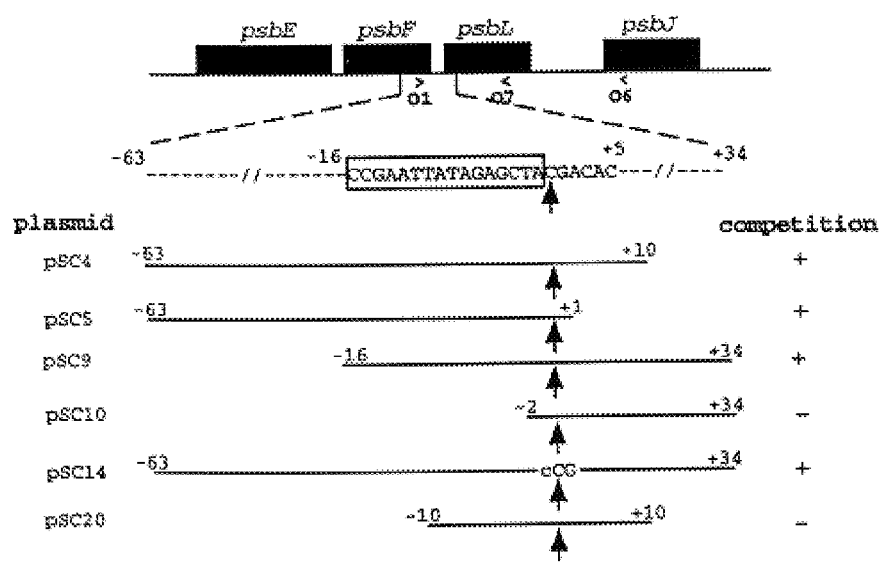
FIGS. 9A and 9B depict a partial DNA map and a series of autoradiograms illustrating the existence of competition for the psbL-specific transfactor (psbL-SEF) in the transgenic plants.
Figure 9B:
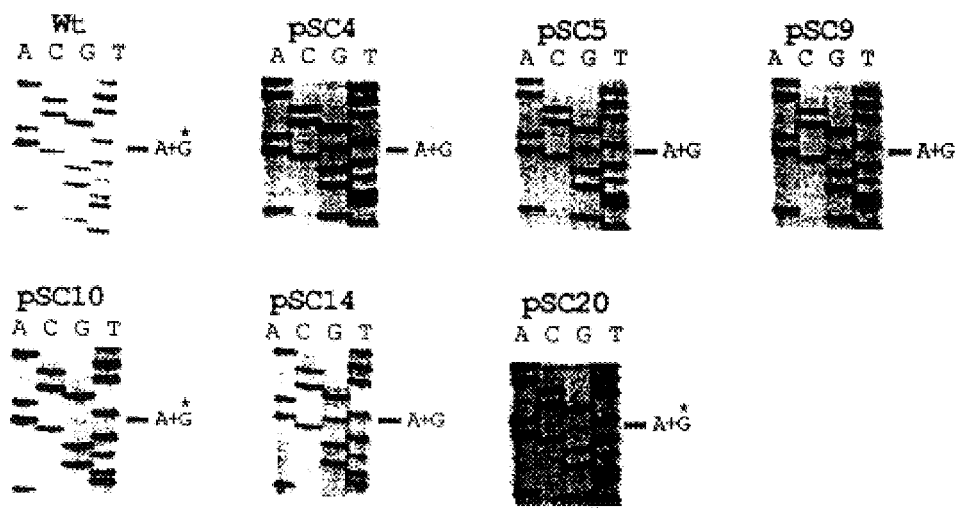

Testing psbL editing efficiency in plastids expressing the chimeric ΔpsbF/ΔpsbL deletion derivatives, shown in FIGS. 7A and 7B, was used to further define psbL sequences which interact with psbL-SEF. Out of the 22 nucleotides minimally required for editing, only the segment upstream of the editing site was able to compete with endogenous psbL for psbL-SEF. The 16 nt psbL-SEF binding site (boxed) within the 22 nt psbL editing recognition sequence (SEQ ID NO: 10) is shown in FIG. 9A. sequences between nucleotides −16/−10 are critical for competition since competition is abolished in plastids containing the pSC20 construct which lacks this sequence. See FIG. 9B. Interestingly, the plants expressing the pSC14 construct with the A to C mutation at position −1 also maintained competition, although this mutation completely abolished editing. The psbL editing efficiency data for the critical constructs are shown in FIGS. 9A and 9B. While in the wildtype plants psbL mRNA is >99% edited, competition in the transgenic lines lead to accumulation of a significant amount of unedited psbL transcript.

D. Editing of the ndhD Initiation Codon in Chimeric mRNA

Figure 10A:
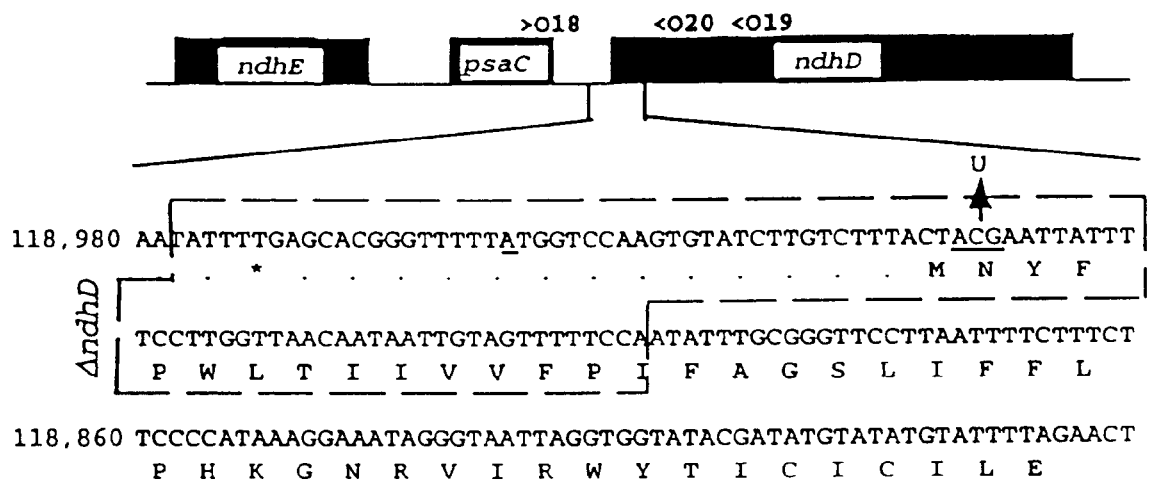
FIGS. 10A, 10B and 10C show a partial DNA map and a series of autoradiograms illustrating that chimeric mRNAs containing the ndhD editing site do not compete for psbL-SEF.
Figure 10B:
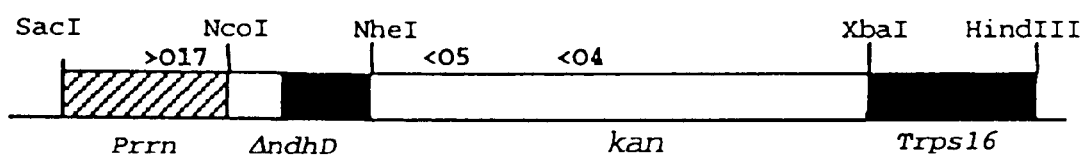

Sequence analysis of ndhD and the corresponding cDNA by Neckermann et al (1994) has established that the ndhd translation initiation codon is created by editing of an ACG codon to an AUG codon in tobacco, spinach and snapdragon. The following experiments were designed to test whether ndhD editing requires a depletable trans-factor as found for psbL, and whether this trans-factor is utilized for the editing of both initiation codon sites. For this purpose, an 89 nucleotide fragment (−48/+40) spanning the ndhD editing site was translationally fused with the kan coding region and cloned in a Prrn/Trpsl6 expression cassette. See FIGS. 10A 10B and 10C. The chimeric genes were constructed by N-terminal fusion of PCR amplified sequences from the tobacco ndhD gene (NcoI/NheI fragments) to bacterial kan gene lacking the initiation codon (NheI/XbaI fragments). For a detailed description of the construction of the chimeric gene see Example II, section A. The chimeric gene was introduced into the tobacco plastid genome by linkage to a spectinomycin resistance gene. In the chimeric gene, expression of the ΔndhD/kan fusion protein was dependent on the editing of the ndhD site. To prevent translation from an upstream AUG, a point mutation was introduced 26 nt upstream of the editing site changing an A to a C, underlined in FIG. 10A (SEQ ID NO: 11).

Figure 10C:
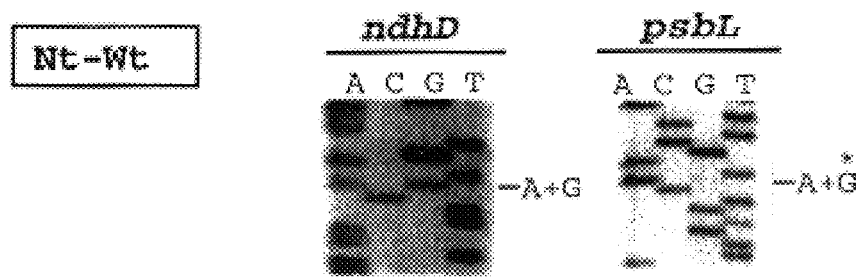
Figure 10C:
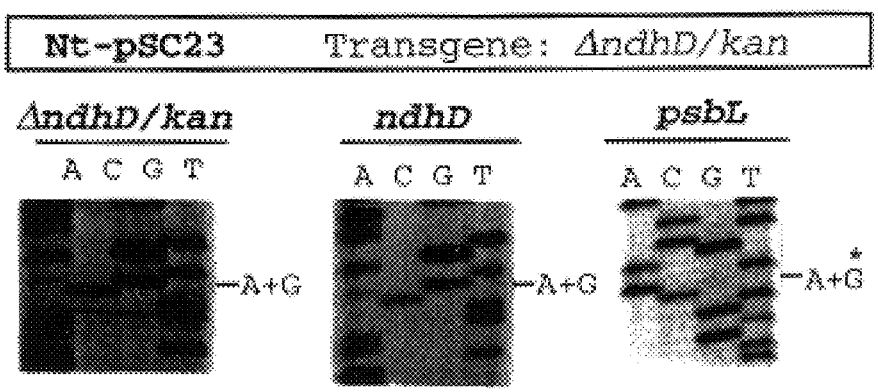
Figure 10C:
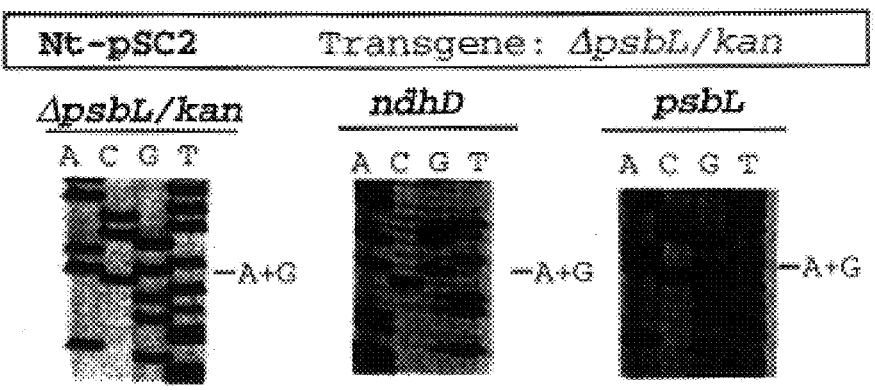

Nt-pSC23 plants expressing the ΔndhD/kan protein were resistant to kanamycin indicating editing of the ndhD site. Direct sequencing of PCR amplified ΔndhD/kan revealed a very low efficiency (~7%) of editing, shown in FIG. 10C. The ndhD transcript in the wild-type plants is edited at significantly higher efficiency (~45%), which is reduced in the Nt-pSC23 plants to ~20%. See FIG. 10C. The reduction in the editing efficiency of the endogenous ndhD transcript in the transgenic plants indicates that increasing the demand for ndhD editing leads to the depletion of an editing factor which is present in limiting amounts. However, the efficiency of editing of the psbL transcript in the transgenic Nt-pSC23 plants was comparable to the wild-type levels, >99%, shown in FIG. 10C. Since psbL editing in the Nt-pSC23 plants is unaffected, the depleted editing factor is ndhD-specific, and is not required for psbL editing.

ndhD editing in plants expressing the chimeric kan gene fused with the 98 nt ΔpsbF/ΔpsbL fragment (SEQ ID NO: 1), Nt-pSC2, FIGS. 7A and 7B, was also examined. In such plants reduced editing of the endogenous psbL mRNA due to competition for psbL-SEF has been shown (Chaudhuri et al., 1995; FIG. 10C). However, in the same plants the endogenous ndhD editing is unaffected, see FIG. 10C, indicating that psbL-SEF is not involved in editing the ndhD site.

Discussion

The above examples describe the analysis of the cis-element requirements for mRNA editing in plastids. The data show that the C to U conversion in the psbL mRNA is directed by a 22 nucleotide sequence (SEQ ID NO: 10) which encompasses 16 nucleotides upstream and 5 nucleotides downstream of the edited C at position 0. The 22 nt sequence (SEQ ID NO: 10) is conserved in tobacco, spinach (Kudla et al., 1992) and bell pepper (Kuntz et al., 1992), species in which editing of the psbL translation initiation codon has been reported.

The role of nucleotides directly flanking the editing site was tested by mutating them in the 98 nt ΔpsbF/ΔpsbL fragment (SEQ ID NO: 1) which is efficiently edited. Changing the upstream A at −1 to a C completely abolished editing of the correct C. However, changing the G at +1 to a C allowed editing of the correct C, although at a reduced efficiency. Editing of the correct C in the mutated ACC codon indicates the high fidelity of nucleotide selection for editing. This is consistent with the observation that specific C nucleotides are edited within flanking C sequences (Kossel et al., 1993; Maier et al., 1995). Furthermore, editing of the ACC codon suggests that translation initiation is not required for editing to occur, providing direct evidence for the lack of linkage between translation and editing. This finding is consistent with mRNA editing in plastids lacking ribosomes (Zeltz et al., 1993) and with editing of unspliced plastid mRNAs which are not translatable (Freyer et al., 1993).

The psbL translation initiation codon is only one of the approximately 25 editing sites found in the plastids of higher plants (Maier et al., 1995). Further studies will be required to determine how typical is the close proximity of cis-sequences to the editing sites in plastids found for psbL. In this regard, the ndhD initiation codon appears to be similar since all information required for editing is contained in a relatively small (98 nt) RNA segment. However, editing of sites II and III in the tobacco ndhB gene (Maier et al., 1992) requires sequences further away than 150 nucleotides (S.C. and P.M., unpublished). Therefore, localization of editing cis sequences is not uniform, in line with the proposed individual recognition mechanism for each of the ~25 plastid editing sites.

Individual recognition of the editing sites is consistent with the finding that site-specific trans-factors are depleted by over-expression of the psbL and ndhD target RNAs. While ACG to AUG editing in both transcripts creates a translation initiation codon, over-expression of either of the target RNAs affects the editing efficiency of only the source mRNA.

It is likely that C to U editing in plastids involves cytidine deamination, as shown for plant mitochondria (Yu and Schuster, 1995). Editing therefore minimally involves either a single polypeptide containing both a site-specific recognition domain and a deaminase domain, or a complex containing at least two components, one providing site-specific recognition and the other with cytidine deaminase activity. Such a multi-component complex consisting of cytidine deaminase (APOBEC-1) and auxiliary proteins has been shown to be involved in C to U editing of the mammalian nuclear apolipoprotein B mRNA. In addition to the common occurrence of C to U editing, close clustering of the cis-sequences around the editing site is an additional feature shared by the plastid psbL and the mammalian nuclear apolipoprotein B editing systems. Editing of apolipoprotein B is directed by an 11 nucleotide recognition sequence located four nucleotides downstream of the editing site. In addition, sequences upstream are required for efficient editing (reviewed in Innerarity et al., 1996). However, in contrast to editing of psbL, recognition specificity of the apolipoprotein B editing process is relaxed, since cytosines introduced adjacent to the edited nucleotide may also be modified (Chen et al., 1990).

EXAMPLE III

Editing Based Δrpl2/kan Selectable Marker Gene

Figure 11:
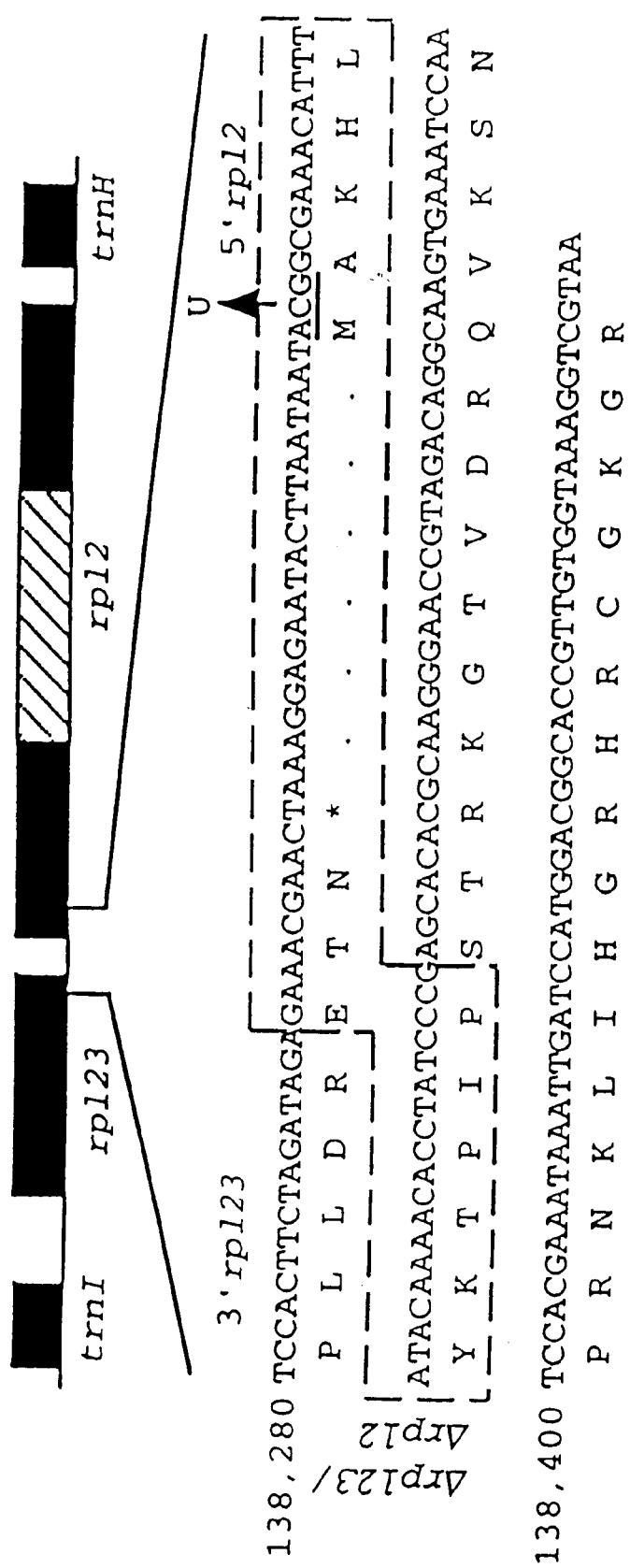
FIGS. 11A and 11B show a schematic illustration of the Δrpl2/kan gene. A partial map of the maize plastid genome containing the trnI, rpl23, rpl2 and trnH genes, and the DNA sequence (SEQ ID NO: 13) with the edited rpl2 translation initiation codon (underlined) is shown in FIG. 11A. The genes are marked and the DNA sequence (SEQ ID NO: 13) is numbered according to Maier et al., 1995. The Δrpl2 segment in a dashed box was translationally fused with the kan gene, as shown in FIG. 11B.
Figure 11:
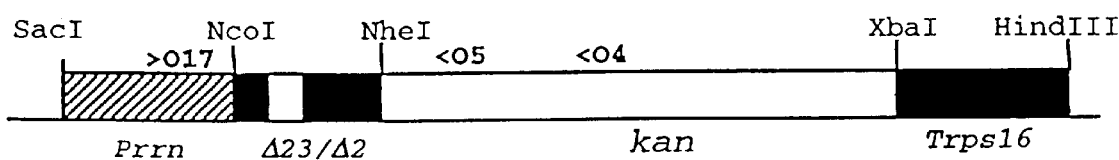

The chimeric Δrpl2/kan gene was constructed by N-terminal fusion of PCR amplified sequences from the maize rpl2 gene (NcoI/NheI fragment; 5'primer: 5'-CTAGCCATGGAAACGAACTAAAGGAGAATAC-3' (SEQ ID NO: 53); 3' primer: 5'-CTAGCTAGCCGGGATAGGTGTTTTGTATAAA-3' (SEQ ID NO: 54)) to a bacterial kan gene lacking the initiation codon (NheI/XbaI fragments). See FIGS. 11A and 11B. The chimeric genes were then cloned in NcoI/XbaI digested plasmid pLAA24A (Zoubenko et al., 1994), as described for the construction of ΔpsbL/kan genes and introduced into the tobacco plastid genome (Chaudhuri and Maliga, 1996). The chimeric mRNA was transcribed in tobacco plastids. In tobacco, no editing of the maize rpl2 translation initiation codon was found. Also, the transformed plants were sensitive to kanamycin. However, editing of this chimeric gene will occur in rice, maize and other cereals in which the rpl2 translation initiation codon is created by editing.

EXAMPLE IV

Conversion of Internal Editing Sites to Edited Translation Initiation Codons

The translation initiation codon is created by conversion of an ACG codon to an AUG codon in the psbL, ndhD and rpl2 plastid mRNAs. The psbL (Kudla et al., 1992) and ndhD (Neckermann et al., 1994) editing sites are present in a few but not all dicotyledonous species, whereas the rpl2 site is edited in most but not all cereals (Hoch et al., 1991). The maize rpl2 site is not edited in tobacco (Chauduri and Maliga, see Example III). Therefore, the psbL, and ndhD editing sites are useful to create editing-based marker genes in some dicots, and rpl2-based chimeric genes are useful in most monocots.

There are many more examples for the editing of internal codons than for editing of translation initiation codons. However, translation initiation is not required for editing of codons in the psbL sequence context (Chaudhuri and Maliga, 1996). Based on these results, internal codons may also serve as translation initiation codons as long as editing creates a translatable mRNA. There is a high frequency of Ser to Phe, Ser to Leu and Pro to Leu transitions, and a lower extent of Thr to (F)Met transitions. Given that U and A are relatively frequent at the first nucleotide position, editing of UCG codons will be maintained in most editing contexts even if the first nucleotide is changed to A to create a codon which may be edited to a translation initiation codon by C to U conversion. Good candidates for such mutagenesis are editing Sites I and II of the rpoB mRNA, which are widely edited in both dicots and monocots (Zeltz et al., 1993).

Figure 12:
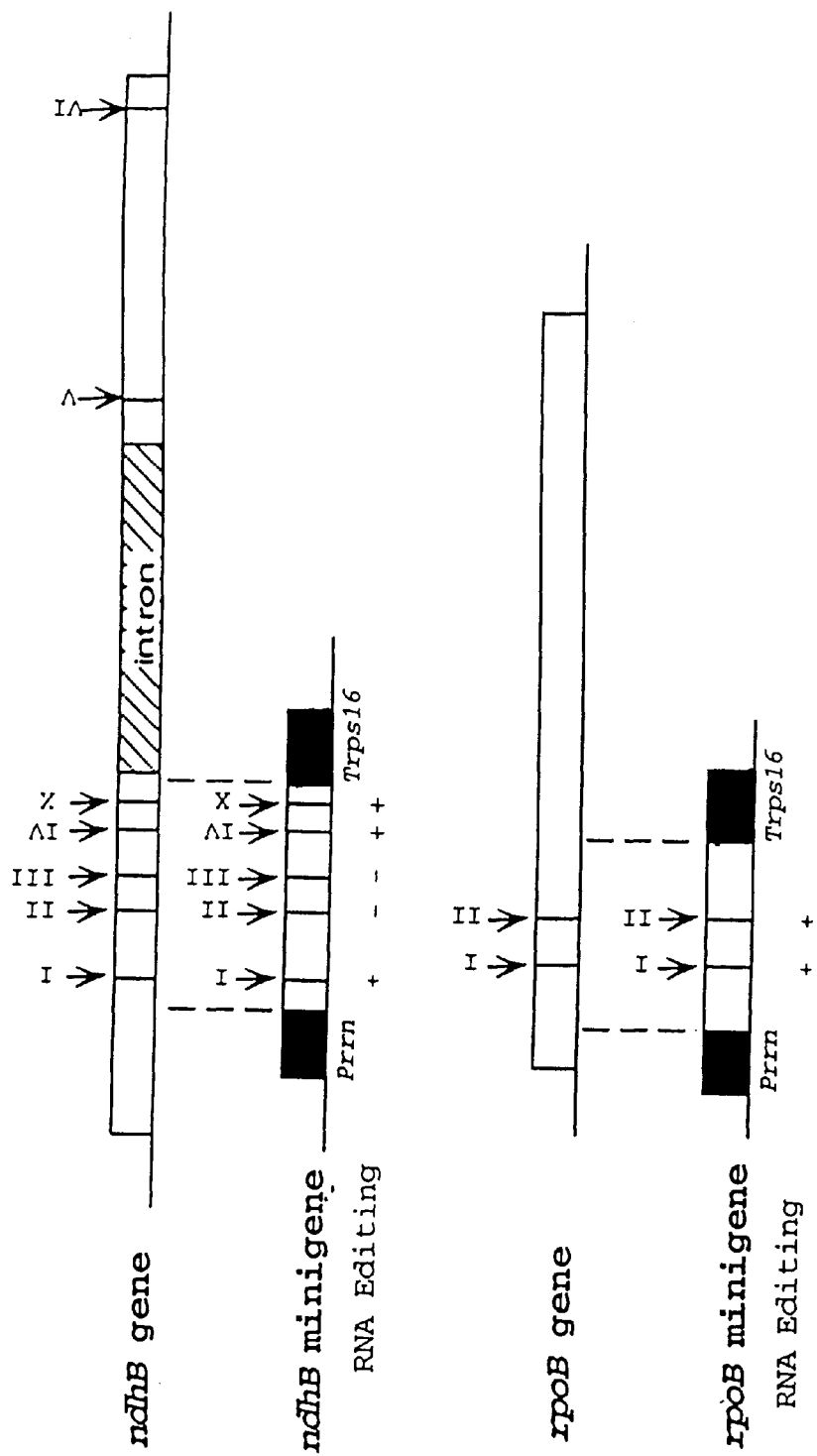
FIG. 12 is a schematic drawing of minigenes used to test editing in segments of ndhB and rpoB RNAs. The nhdB plastid gene and its minigene are shown in the upper portion of FIG. 12 and the rpoB plastid gene and its corresponding minigene (lower portion of FIG. 12) are shown. Editing sites are indicated in the Figure. Minigene RNAs are expressed in a cassette which contains the rRNA operon promoter (Prrn) and the 3' untranslated region of the rps16 ribosomal protein gene (Trps16) required for mRNA stability (Zoubenko et al., 1994). The editing sites and the references are listed in Table IV.

RNA sequences required to direct editing may be contained within a short segment adjacent to the editing site as in the case of the psbL gene or may be at a distance as in case of Sites II and III of the ndhB gene (Chaudhuri and Maliga, 1996). Editing has been tested in ndhB and rpoB minigenes to identify editing sites that are useful for the construction of chimeric genes.

ndhB and rpoB editing sites have been identified for which the relevant cis-sequences are within a short segment. These short gene segments have been incorporated in chimeric genes, expressed in tobacco plastids, and tested for editing by direct sequencing of the PCR-amplified transgene cDNAs. The editing sites in the source genes are listed in Table IV. The map of the ndhB and rpoB minigene derivatives is shown in FIG. 12.

TABLE IV

RNA editing in ndhB and rpoB minigenes

| Editing site | Codon No | Codon (amino acid) Unedited/Edited | Reference |
|---|---|---|---|
| rpoB site I | 158 | [a]TCG (Ser) to TTG (Leu) | Zeltz et al., 1993 |
| rpoB site II | 184 | TCA (Ser) to TTA (Leu) | Zeltz et al., 1993 |
| ndhB site I | 156 | CCA (Pro) to CTA (Leu) | Maier et al., 1992 |
| ndhB site II | 196 | CAT (His) to TAT (Tyr) | Maier et al., 1992 |
| ndhB site III | 204 | TCA (Ser) to TTA (Leu) | Maier et al., 1992 |
| ndhB site IV | 246 | CCA (Pro) to CTA (Leu) | Maier et al., 1992 |
| ndhB site X | 249 | TCT (Ser) to TTT (Phe) | Kossel, H. (personal comm.) |

[a]In tobacco, a TCA codon is edited to a TTA codon (Chaudhuri et al., 1995).

The ndhB minigene contains an ndhB fragment which is 369 nucleotide in size (between nucleotides 143,174 and 144,042 of the plastid genome, Shinozaki et al., 1986). It contains some of the first exonic sequence including five editing sites, named as sites I, II, III, IV and X. Sites I, II, III and IV are edited in maize, rice and tobacco (Maier et al., 1992). Therefore, marker genes based on the editing of these sites will be useful in a broad range of crops, including monocots and dicots. Site X is edited in tobacco only (Kossel, H., personal communication), therefore this site is less useful for the construction of chimeric marker genes.

In the ndhB minigene, the truncated coding region is expressed in the original reading frame, in the Prrn-Trps16 cassette. This was achieved by introducing an NcoI site at the 5'-end of the truncated reading frame, which includes the translation initiation codon (CCATGG) from which the minigene RNA can be translated from translation signals contained in the cassette. The minigene contains the DNA sequence ATGGCAGCTACT (SEQ ID NO: 55) downstream of the translation initiation codon; nucleotide C at position five corresponds to nucleotide 143,674 in the plastid genome. In addition, during PCR amplification, an in-frame stop codon was introduced at the 3'-end of the truncated coding region. (5' PCR primer: 5'-CTAGCCATGGCAGCTACTCTAGGGGGAATG-3' SEQ ID NO: 56; 3' PCR primer: 5'-CTAGTCTAGACGTATACGTCAGGAGTCCA-3' SEQ ID NO: 57). The minigene was physically linked to a selectable spectinomcyin resistance (aadA) gene in a suitable plastid targeting vector and the vector DNA was introduced into tobacco leaf chloroplasts by the biolistic process. Transplastomes with the integrated, linked transgenes were selectively amplified by incubating the bombarded leaf segments on a spectinomycin medium, on which transgenic shoots were directly regenerated. The protocols for plastid transformation have been described in Svab and Maliga, 1993 and Zoubenko et al., 1994.

Out of the five sites, Sites I, IV and X were highly edited in the minigene. This finding indicates, that the cis sequences required for editing are located relatively close to the editing sites, as was shown for the psbL translation initiation codon (Chaudhuri and Maliga, 1996). Furthermore, cis sequences for Sites I and IV are suitable for inclusion in marker genes with utility in both dicots and monocots, since the capacity for editing is present in these widely divergent taxonomic groups. Interestingly, ndhB Sites II and III were not edited in the minigene, indicating that the cis sequences required for editing are further away than +/−150 nucleotides from the editing site. Therefore, cis sequences required for editing are not uniformly positioned relative to the editing site.

The rpoB minigene contains a 281 nucleotide fragment of the rpoB gene, encoding the RNA polymerase β-subunit. The fragment contains two editing sites (I, II, see Table IV and FIG. 12; based on Zeltz et al., 1993). Both editing sites are present in maize, rice, barley, spinach and tobacco (Maier et al., 1992). The rpoB minigene was constructed and introduced into plastids as described for the ndhB minigene. The minigene contains the DNA sequence ATGGTCCCGGT (SEQ ID NO: 58) downstream of the translation initiation codon; nucleotide G at position four corresponds to the complement of nucleotide 27120 in the plastid genome (Zhinozaki et al., 1986). The rpoB fragment for the minigene construction was obtained by PCR amplification (5' PCR primers: 5'-CTAGCCATGGGTCCCGGTATTTATTACCG-3' SEQ ID NO: 59; 3' PCR primer: 5'-CTAGGTCGACTTAGGCATTTTCTTTTGACCCAAT-3' SEQ ID NO: 60). Transgenic plants representing several independently transformed lines were obtained and assayed for editing. Complete editing of both of the sites was found in the minigenes by sequencing PCR-amplified cDNAs. Given the presence of these sites in both monocots and dicots, marker genes based on the editing of either of these sites could be used in a wide variety of crops.

EXAMPLE V

RNA Editing for Tissue-specific Regulation of Foreign Gene Expression

RNA editing in plastids was discussed assuming that editing is constitutive, and facilitates expression of marker genes in all tissue types. It is known, however, that environmental and developmental conditions significantly affect editing efficiency (Bock et al., 1993; Hirose et al., 1996). Tissue specific differences in editing efficiency facilitate the design of chimeric genes the translation of which is dependent on tissue type due to tissue-specific conversion of ACG codons to a translation initiation codon. Such chimeric genes are useful when accumulation of an economically useful protein, such as an insecticidal endotoxin is desired only in specific tissue types, such as leaves, root hairs, root cortex or epidermis cells.

Alternatively, desired tissue-specific expression of economically useful genes may be obtained when editing tissue specifically creates a translation termination (stop) codon. Formation of stop codons by editing may be readily obtained by engineering in plastids. For example, a stop codon in plastids is created when changing the reading frame of the psbL editing site. Normally, the psbL translation initiation codon is created by C to U conversion in the ACGA sequence. Moving the reading frame by one nucleotide, editing creates the TGA stop codon. Editing of the first C nucleotide of a codon is also known, such as Site II of the ndhB transcript (Maier et al., 1992). Therefore, C to U editing of the CAA codon will create the TAA translation termination codon.

Most plastid genes are organized in polycistronic transcription units. Therefore, polycistronic transcription units may be built for simultaneous expression of multiple proteins. An example for a dicistronic transcription unit, from which two proteins are simultaneously expressed was obtained by engineering of the plastid genome (Staub and Maliga, 1995). Tissue-specific expression of such polycistronic mRNAs may be obtained by making the translation dependent on RNA editing, either through creation of a translation initiation codon, or by terminating translation.

REFERENCES

1. Araya, A., Domec, C., Begu, D., and Litvak, J. (1992) an in vitro system for editing of ATP synthase subunit mRNA using wheat mitochondrial extracts. *Proc. Natl. Acad. Sci. USA*, 89, 1040–1044.
2. Benne, R. (1994) RNA editing in trypanosomes. *Eur. J. Biochem.* 221, 9–23.
3. Bachmann, B., Lueke, W. and Hunsmann, G. (1990) Improvement of PCR amplified DNA sequencing with the aid of detergents. *Nucleic Acids Res.*, 18, 1309.
4. Bock, B., Hagemann, R., Kossel, H and Kudla, J (1993) Tissue- and stage-specific modulation of RNA editing of the psbF and psbL transcript from spinach plastids—a new regulatory mechanism? *Mol. Gen. Genet.*, 240, 238–244.
5. Bock, R., and Maliga, P. (1995) In vivo testing of a tobacco plastid DNA segment for guide RNA function in psbL editing. *Mol. Gen. Genet.*, in press.
6. Bock, R., Kossel, H. and Maliga, P. (1994) Introduction of a heterologous editing site into the tobacco plastid genome: the lack of RNA editing leads to a mutant phenotype. *EMBO J.*, 13, 4623–4628.
7. Bonnard, G., Gualberto, J. M. (1992) RNA editing in plant mitochondria. *Critical Reviews in Plant Sciences*, 10, 503–524.
8. Carillo, N., Seyer, P., Tyagi, A. and Herrmann, R. G. (1986) Cytochrome b-559 genes from Oenothera hookeri and Nicotiana tobacco show a remarkably high degree of conservation as compared to spinach. The enigma of cytochrome b-559: Highly conserved genes and proteins but no known function. *Curr. Genet.*, 10, 619–624.

9. Carrer, H., Hockenberry, T. N., Svab, Z. and Maliga, P. (1993) Kanamycin resistance as a selectable marker for plastid transformation in tobacco. *Mol. Gen. Genet.*, 241, 49–56.
10. Carrer, H., Staub, J. M. and Maliga, P. (1991) Gentamicin resistance in Nicotiana conferred by AAC(3)-I, a narrow substrate specificity acetyltransferase. *Plant Mol. Biol.*, 17, 301–303.
11. Chan, L. (1993) RNA editing: exploring one mode with apolipoprotein B mRNA. *BioEssays* 15, 33–41.
12. Chaudhuri, S. and Maliga, P. (1996) Sequences directing to C to U editing of the plastid psbL mRNA are located within a 22 nucleotide segment spanning the editing site. *EMBO J.*, accepted, pending on revisions.
13. Chaudhuri, S., Carrer, H. and Maliga, P. (1995) Site-specific factor involved in the editing of the psbL mRNA in tobacco plastids. *EMBO J.* 14, 2951–2957.
14. Cornelissen M, Vandewiele M. (1989) Nuclear transcriptional activity of the tobacco plastid psbA promoter. *Nucleic Acids Res.* 17:19–29.
15. Freyer, R., Hock, B., Neckermann, K., Maier, R. M. and Kössel, H. (1993) RNA editing in maize chloroplasts is a processing step independent of splicing and cleavage to monocistronic mRNAs. *The Plant J.*, 4, 621–629.
16. Gray, M. W. and Covello, P. S. (1993) RNA editing in plant mitochondria and chloroplasts. *FASEB J.*, 7, 64–71.
17. Hanson, M. R., Sutton, C. A. and Lu, B. (1995) Plant organelle gene expression: altered by RNA editing. *Trends in plant Sciences*, 1, 57–64.
18. Higuchi, M., Single, F. N., Kohler, M., Sommer, B., Sprengel, R. and Seeburg, P. H. (1993) RNA editing of AMPA receptor subunit GluR-B: a base-paired intron-exon structure determines position and efficiency. *Cell*, 75, 1361–1370.
19. Hirose, T, Fan, H, Suzuki, Y. Y., Wakasugi, T., Tsudzuki, T., Kossel, H. and Sugiura, M. (1996) Occurrence of silent RNA editing in chloroplasts: its species specificity and the influence of environmental and developmental conditions. *Plant Mol. Biol.* 30:667–672.
20. Hock, B., Maier, R. M., Appel, K., Igloi, G. L. and Kossel, H. (1991) Editing of a chloroplast mRNA by creation of an initiation codon. *Nature* 353: 178–180.
21. Hodges, P. and Scott, J. (1993) Editing of mammalian apolipoprotein B mRNA by site-specific RNA deamination. In Benne, R. (ed.), RNA editing. *The alteration of protein coding sequences of RNA*. Ellis Horwood, New York, N.Y., pp. 125–151.
22. Innerarity, T. L., Boren, J., Yamanaka, S. and Olofsson, S. O. (1996) Biosynthesis of apolipoprotein B48-containing lipoptotiens. *J. Biol. Chem.*, 271, 2353–2356.
23. Koncz, C. S., Martini, N., Mayerhofer, R., Konca-Kalman, Z. S., Korber H., Redei, G. Y., Schell, J., (1989) High-frequence T-DNA-mediated gene tagging in plants. *Proc. Natl Acad. Sci. USA* 86:8467–8471.
24. Kossel, H., Hoch, B., Maier, R. M., Igloi, G. L., Kudla, J., Zeltz, P., Freyer, R., Neckermann, K. and Ruf, S. (1993) RNA editing in chloroplasts. In Kueck, U. and Brennicke, A. (eds.), *Plant Mitochondria*. VCH Publishers, Weinheim, Germany, pp. 93–102.
25. Kudla, J., Igloi, G. L., Metzlaff, M., Hagemann, R. and Kossel, H. (1992) RNA editing in tobacco chloroplasts leads to the formation of a translatable psbL messenger RNA by a C-to-U substitution within the initiation codon. *EMBO J.*, 11, 1099–1103.
26. Kuntz, M., Camara, B., Weil, J. H. and Schantz, R. (1992) the psbL gene from bell pepper (*Capsicum annuum*): plastid RNA editing occurs in non-photosynthetic chromoplasts. *Plant. Mol. Biol.* 20, 1185–1188.
27. Maier, R. M., Neckermann, K., Hoch, B., Akhmedov, N. B. and Kossel, H (1992) Identification of editing positions in the ndhB transcript from maize chloroplasts reveals sequence similarities between editing sites of chloroplasts and plant mitochondria. *Nucl. Acids Res.*, 20, 6189–6194.
28. Maier, R. M., Neckermann, K., Igloi, G. L. and Kossel, H. (1995) Complete sequence of the maize chloroplast genome: gene content, hotspots of divergence and fine tuning of genetic information by transcript editing. *J. Mol. Biol.* 251, 614–628.
29. Maliga, P (1995) Biolistic transformation of tobacco cells with nuclear drug resistance genes. In Maliga, P., Klessig, D., Cashmore, A., Gruissem, W. and Varner, J. (eds), Methods in Plant Molecular Biology—A Laboratory Manual. Cold Spring Harbor Press, pp. 73–54.
30. Maliga, P. (1993) Towards plastid transformation in flowering plants. *Trends Biotechnol.*, 11, 101–106.
31. Mettler, I. J. (1987) A simple and rapid method for minipreparation of DNA from tissue cultured plant cells. *Plant Mol. Biol. Rep.*, 5, 346–349.
32. Murashige, T. and Skoog, F. (1962) A revised medium for rapid growth and bioassays with tobacco tissue culture. *Physiol. Plant.*, 15, 473–497.
33. Neckermann, K., Zeltz, P., Igloi, G. L., Kössel, H., and Maier, R. M. (1994) The role of RNA editing in convervation of start codons in chloroplast genomes. *Gene*, 146, 177–182.
34. Sarkar, G. and Sommer, S. S. (1990) The "megaprimer" method of site-directed mutagensis. *Biotechniques* 8, 404–407.
35. Schuster, W. and Brennicke, A. (1994) The plant mitochondrial genome: physical structure, information content, RNA editing, and gene migration. *Annu. Rev. Plant Physiol. Plant Mol. Biol*, 45, 61–78.
36. Schuster, W. and Brennicke, A. (1994) The plant mitochondrial genome: physical structure, information content, RNA editing, and gene migration. *Annu. Rev. Plant Physiol. Plant Mol. Biol.*, 45, 61–78.
37. Scott, J. (1995) A place in the world for RNA editing. *Cell*, 81, 833–836.
38. Shinozaki, K. et al. (1986) The complete nucleotide sequence of the tobacco chloroplast genome: Its gene organization and gene expression. *EMBO J.*, 5, 2043–2049.
39. Simpson, L., Maslov, D. A. and Blum, B. (1993) RNA editing in Leishmania mitochondria. In Benne, R. (ed.), RNA editing. The alteration of protein coding sequences of RNA. Ellis Horwood, New York, N.Y., pp. 53–85.
40. Staub, J. and Maliga, P. (1994) Translation of psbA mRNA is regulated by light via the 5'-untranslated region in tobacco plastids. *Plant J.*, 6, 547–553.
41. Sutton, C. A., Zoubenko, O. V., Hanson, M. R. and Maliga, P. (1995) A plant mitochondrial sequence transcribed in transgenic tobacco chloroplasts is not edited. *Mol. Cell. Biol.* 15, 1377–1381.
42. Svab, Z. and Maliga, P (1993) High-frequency plastid transformation in tobacco by selection for a chimeric aadA gene. *Proc. Natl. Acad. Sci. USA*, 90, 913–917.
43. Teng, B. B., Burant, C. F., Davidson, N. O. (1993) Molecular cloning of the apolipoprotein B messenger RNA editing protein. *Science*, 260, 1816–1819.
44. Yu, W. and Schuster, W. (1995) Evidence for a site-specific cytidine deamination reaction involved in C to U editing of plant mitochondria. *J. Biol. Chem.*, 270, 18227–18233.

45. Zeltz, P., Hess, W. R., Neckermann, K., Boerner, T. and Kossel, H. (1993) Editing of the chloroplast rpoB transcript is independent of chloroplast translation and shows different patterns in barley and maize. *EMBO J.,* 12, 4291–4296.
46. Zoubenko, O. V., Allison, L. A., Svab, Z. and Maliga, P. (1994) Efficient targeting of foreign genes into the tobacco plastid genome. *Nucleic Acids Res.,* 22, 3819–3824.

While certain preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A recombinant chimeric DNA construct useful for selection of plastid transformants comprising an edited plastid gene segment translationally fused to the coding region of a selectable marker gene, said selectable marker gene being expressible following RNA editing of said plastid gene segment in plastids comprising said construct.

2. The DNA construct of claim 1, wherein said edited plastid gene segment is selected from the group consisting of psbL, ndhD, rpoB, ndhB and rpl2.

3. The DNA construct of claim 1, wherein said selectable marker gene is selected from the group of genes conferring resistance to kanamycin, gentamycin, hygromycin, methotrexate, spectinomycin, bleomycin, phleomycin, blasticidin, sulfonamide, phosphinothricin, chlorsulfuron, bromoxymil, glyohosate, 2,4Datrazine, 2,2-DCPA, 4-methyl-tryptophane, nitrate, S-aminoethyl-L-cysteine, lysine/threonine, and aminoethyl-cysteine.

4. The chimeric DNA construct of claim 1, which includes edited psbL translationally fused to kan.

5. The chimeric DNA construct of claim 1, which includes edited psbL translationally fused to aadA.

6. The chimeric DNA construct of claim 1, which includes edited ndhD translationally fused to kan.

7. The chimeric DNA construct of claim 1, which includes edited rp12 translationally fused to kan.

8. A vector comprising the construct of claim 1, containing homologous DNA sequences necessary for plastid directed transformation.

9. A vector as in claim 8 further comprising a foreign gene of interest to beneficially augment the phenotype of a plant containing said vector.

10. A chimeric DNA construct comprising an edited segment selected from ndhB sites I, IV or V cloned upstream from a selectable marker gene.

11. A chimeric DNA construct comprising an edited segment selected from rpoB sites I or II cloned upstream from a selectable marker gene.

12. A method for selection of transplastomic lines comprising:
   a) transforming plastids in a sample with a chimeric DNA construct comprising an edited gene segment translationally fused to the coding region of a selectable marker gene, said selectable marker gene being expressible following RNA editing of said gene segment;
   b) culturing said sample in medium containing a selective agent facilitating identification of transformed plastids; and
   c) selecting and propagating cells expressing said selectable marker; thereby selecting transplastomic lines.

13. The method of claim 12, wherein said chimeric DNA construct is incorporated into a vector containing homologous DNA sequences necessary for plastid directed transformation.

14. The method of claim 12 wherein a plant is regenerated from said cells expressing said selectable marker.

15. The method of claim 13, wherein said vector further comprises a foreign gene of interest to beneficially augment the phenotype of said regenerated plant.

16. The method of claim 15, wherein said edited segment is edited in a tissue specific manner such that said foreign gene of interest is expressed in a tissue specific manner.

17. The method of claim 15, for use in monocots or dicots.

* * * * *